US011253205B2

(12) United States Patent
Enari et al.

(10) Patent No.: US 11,253,205 B2
(45) Date of Patent: Feb. 22, 2022

(54) PULSE PRESSURE AND BLOOD PRESSURE ANALYSIS DEVICE, PULSE PRESSURE AND BLOOD PRESSURE ANALYSIS METHOD, AND PROGRAM

(71) Applicant: SEIKO EPSON CORPORATION, Tokyo (JP)

(72) Inventors: Megumi Enari, Shiojiri (JP); Ayae Sawado, Kai (JP); Kohei Yamada, Shiojiri (JP); Akiko Yamada, Shiojiri (JP); Akira Ikeda, Chino (JP); Masayasu Fukuoka, Shiojiri (JP); Akira Kitahara, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 499 days.

(21) Appl. No.: 16/103,968

(22) Filed: Aug. 16, 2018

(65) Prior Publication Data

US 2019/0053768 A1    Feb. 21, 2019

(30) Foreign Application Priority Data

Aug. 16, 2017 (JP) .............................. JP2017-157162
May 31, 2018 (JP) .............................. JP2018-104934

(51) Int. Cl.
*A61B 5/00* (2006.01)
*A61B 5/026* (2006.01)
*A61B 5/021* (2006.01)

(52) U.S. Cl.
CPC .......... *A61B 5/7278* (2013.01); *A61B 5/0261* (2013.01); *A61B 5/02108* (2013.01); *A61B 5/6824* (2013.01)

(58) Field of Classification Search
CPC . A61B 5/7278; A61B 5/02108; A61B 5/6824; A61B 5/0261
(Continued)

(56) References Cited

U.S. PATENT DOCUMENTS

| 5,913,826 A | 6/1999 | Blank |
| 2002/0002339 A1 | 1/2002 | Sugo et al. |

(Continued)

FOREIGN PATENT DOCUMENTS

| JP | 2001-321347 A | 11/2001 |
| JP | 2004-154231 A | 6/2004 |

(Continued)

OTHER PUBLICATIONS

Masaki Goma et al. "The Development of Small Laser Doppler Blood Flow Sensor". Pioneer R&D, vol. 21, No. 1, 2012, pp. 30-36.

(Continued)

*Primary Examiner* — Serkan Akar
*Assistant Examiner* — Renee C Langhals
(74) *Attorney, Agent, or Firm* — Oliff PLC

(57) ABSTRACT

A biological analysis device includes: a pulse pressure calculation unit that calculates a pulse pressure index related to a pulse pressure of a biological body; an average blood pressure calculation unit that calculates an average blood pressure index related to an average blood pressure of the biological body; and a blood pressure calculation unit that calculates a systolic blood pressure and a diastolic blood pressure in accordance with the pulse pressure index and the average blood pressure index. At least one of the pulse (Continued)

pressure index and the average blood pressure index is calculated in accordance with a blood flow index which is calculated from an intensity spectrum related to a frequency of light reflected and received from an inside of the biological body through radiation of a laser beam and is related to a blood flow of the biological body.

9 Claims, 16 Drawing Sheets

(58) Field of Classification Search
USPC .......................................................... 600/480
See application file for complete search history.

(56) References Cited

U.S. PATENT DOCUMENTS

| | | | |
|---|---|---|---|
| 2004/0024295 A1 | 2/2004 | Cook et al. | |
| 2011/0319775 A1 | 12/2011 | Fujii et al. | |
| 2015/0018693 A1* | 1/2015 | Mestha | A61B 5/02427 600/479 |
| 2015/0216458 A1* | 8/2015 | Kasahara | A61B 5/14532 600/316 |
| 2016/0174854 A1* | 6/2016 | Nishida | A61B 5/02007 600/480 |
| 2018/0293797 A1 | 10/2018 | Rana | |
| 2019/0090818 A1* | 3/2019 | Nakajima | A61B 5/0002 |
| 2019/0380598 A1* | 12/2019 | Higuchi | G01N 21/95623 |
| 2020/0276380 A1* | 9/2020 | Maierhofer | A61M 1/3658 |

FOREIGN PATENT DOCUMENTS

| | | | |
|---|---|---|---|
| JP | 2008-018035 A | | 1/2008 |
| JP | 2016-146958 A | | 8/2016 |
| JP | 2016150065 A | * | 8/2016 |
| WO | 2012/142455 A2 | | 10/2012 |
| WO | 2015/199159 A1 | | 12/2015 |
| WO | 2016/130083 A1 | | 8/2016 |

OTHER PUBLICATIONS

U.S. Appl. No. 15/998,545, filed Aug. 16, 2018 in the name of Kohei Yamada et al.
U.S. Appl. No. 15/998,546, filed Aug. 16, 2018 in the name of Ayae Sawado et al.
Sep. 1, 2020 Office Action issued in U.S. Appl. No. 15/998,545.
Sep. 8, 2020 Office Action issued in U.S. Appl. No. 15/998,546.
May 12, 2021 Notice of Allowance issued in U.S. Appl. No. 15/998,546.
Dec. 17, 2020 Office Action issued in U.S. Appl. No. 15/998,545.
Dec. 30, 2020 Office Action ssued in U.S. Appl. No. 15/998,546.
Jul. 28, 2021 Office Action Issued in U.S. Appl. No. 15/998,545.

* cited by examiner

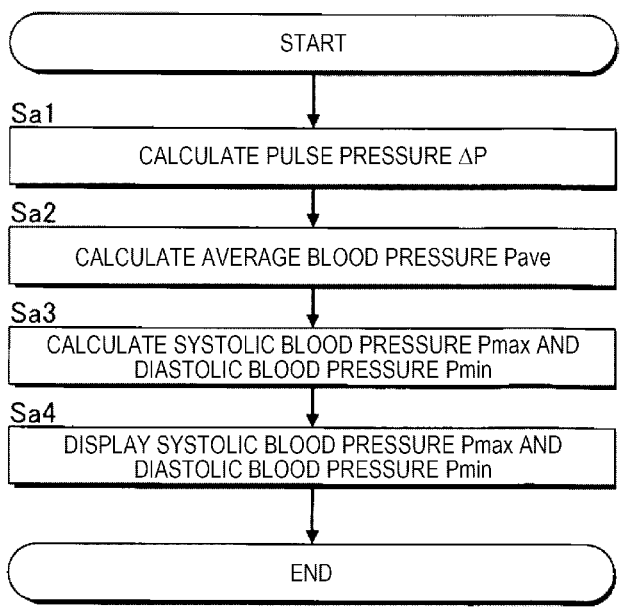
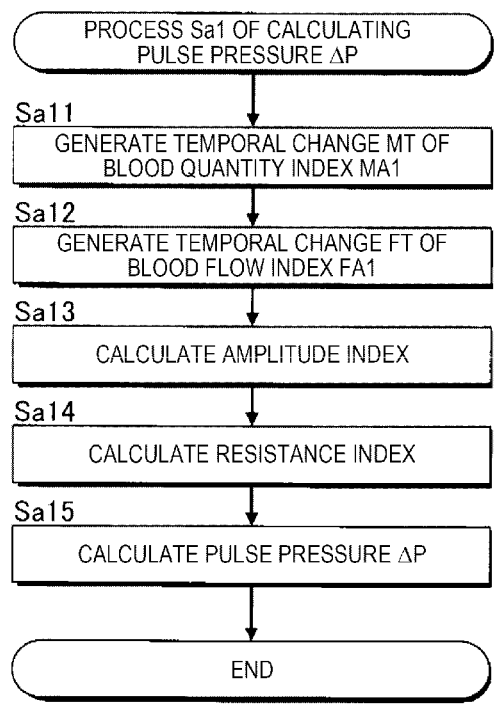

FIG. 26
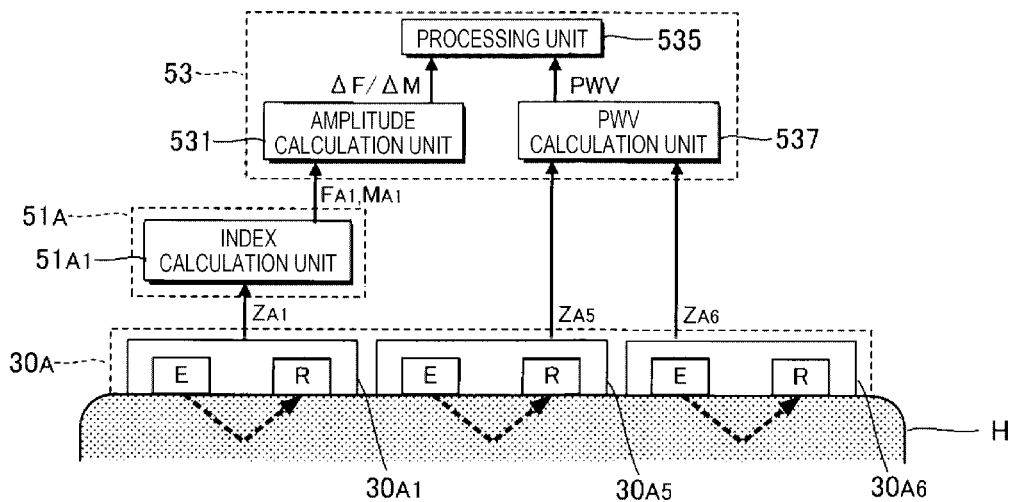
FIG. 27
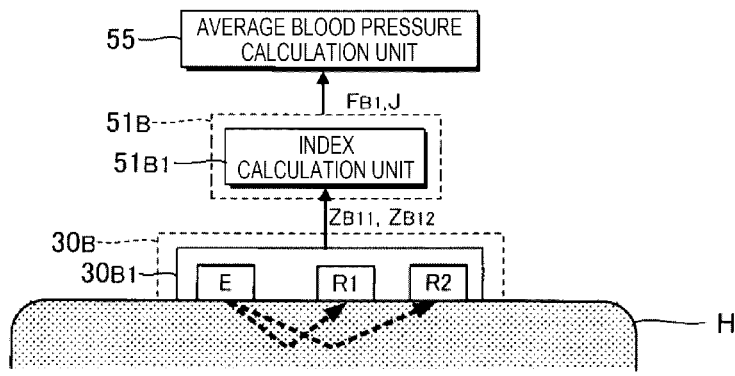
FIG. 28
| | E-R DISTANCE | 1mm | 2mm | 3mm | 4mm | 5mm | 6mm | 7mm |
|---|---|---|---|---|---|---|---|---|
| R1 | DETECTION SIGNAL ZB11 | ○ | ○ | △ | △ | × | × | × |
| R2 | DETECTION SIGNAL ZB12 | × | △ | ○ | ○ | ○ | △ | △ |
○ : HIGH
△ : NORMAL
× : LOW

PULSE PRESSURE AND BLOOD PRESSURE ANALYSIS DEVICE, PULSE PRESSURE AND BLOOD PRESSURE ANALYSIS METHOD, AND PROGRAM

BACKGROUND

1. Technical Field

The present invention relates to a technology for analyzing a biological body.

2. Related Art

Various measurement technologies for analyzing biological information such as blood pressures have been proposed in the related art. For example, JP-A-2004-154231 discloses a blood pressure measurement device that measures a blood pressure using a blood flow rate sensor radiating an ultrasonic wave to a biological body. Specifically, the blood pressure measurement device calculates a systolic blood pressure from a maximum value of an artery diameter and a maximum value of a blood flow rate and calculates a diastolic blood pressure from a minimum value of the artery diameter and a minimum value of the blood flow rate.

However, since noise is included in the calculated value of the artery diameter, a maximum value suitable for the calculation of a systolic blood pressure or a minimum value suitable for the calculation of the diastolic blood pressure may not be specified appropriately in some cases. This is true for a blood flow rate. Accordingly, in the technology of JP-A-2004-154231, a systolic blood pressure and a diastolic blood pressure may not be calculated with high precision.

SUMMARY

A biological analysis device according to a preferred aspect of the invention includes: a pulse pressure calculation unit that calculates a pulse pressure index related to a pulse pressure of a biological body; an average blood pressure calculation unit that calculates an average blood pressure index related to an average blood pressure of the biological body; and a blood pressure calculation unit that calculates a systolic blood pressure and a diastolic blood pressure in accordance with the pulse pressure index and the average blood pressure index. At least one of the pulse pressure index and the average blood pressure index is calculated in accordance with a blood flow index which is calculated from an intensity spectrum related to a frequency of light reflected and received from an inside of the biological body through radiation of a laser beam and is related to a blood flow of the biological body.

A biological analysis method according to a preferred aspect of the invention includes: calculating a pulse pressure index related to a pulse pressure of a biological body; calculating an average blood pressure index related to an average blood pressure of the biological body; and calculating a systolic blood pressure and a diastolic blood pressure in accordance with the pulse pressure index and the average blood pressure index. At least one of the pulse pressure index and the average blood pressure index is calculated in accordance with a blood flow index which is calculated from an intensity spectrum related to a frequency of light reflected and received from an inside of the biological body through radiation of a laser beam and is related to a blood flow of the biological body.

A program according to a preferred aspect of the invention causes a computer to function as: a pulse pressure calculation unit that calculates a pulse pressure index related to a pulse pressure of a biological body; an average blood pressure calculation unit that calculates an average blood pressure index related to an average blood pressure of the biological body; and a blood pressure calculation unit that calculates a systolic blood pressure and a diastolic blood pressure in accordance with the pulse pressure index and the average blood pressure index. At least one of the pulse pressure index and the average blood pressure index is calculated in accordance with a blood flow index which is calculated from an intensity spectrum related to a frequency of light reflected and received from an inside of the biological body through radiation of a laser beam and is related to a blood flow of the biological body.

BRIEF DESCRIPTION OF THE DRAWINGS

The invention will be described with reference to the accompanying drawings, wherein like numbers reference like elements.

FIG. 3 is a diagram illustrating a configuration in which a function of the biological analysis device is focused on.

FIG. 15 is a diagram illustrating a configuration in which elements calculating an average blood pressure are focused on.

FIG. 16 is a flowchart illustrating a biological analysis process executed by a control device.

FIG. 17 is a flowchart illustrating specific content of a process of calculating a pulse pressure.

FIG. 26 is a diagram illustrating a configuration in which elements calculating a pulse pressure are focused on according to a modification example of the first embodiment.

FIG. 27 is a diagram illustrating a configuration in which elements calculating an average blood pressure are focused on according to a modification example of the first embodiment.

FIG. 28 is a table illustrating quality of an SN ratio in a frequency bandwidth used in calculation of a blood flow index in a detection signal and quality of an SN ratio in a frequency bandwidth used in calculation of an absorbance index in a detection signal in a plurality of cases in which a distance between the light-emitting unit and the light-receiving unit is changed.

DESCRIPTION OF EXEMPLARY EMBODIMENTS

First Embodiment

Figure 1:
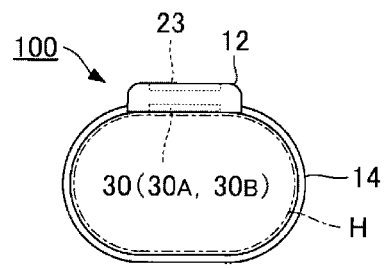
FIG. 1 is a side view illustrating a biological analysis device according to a first embodiment of the invention.

FIG. 1 is a side view illustrating a biological analysis device 100 according to a first embodiment of the invention. The biological analysis device 100 is a measurement instrument that measures biological information of a subject in a non-invasive manner. The biological analysis device 100 according to the first embodiment measures a systolic blood pressure Pmax and a diastolic blood pressure Pmin of a specific part (hereinafter referred to as a "measurement region") H of the body of a subject (user) as biological information. In the following description, a wrist or an upper arm of the subject is exemplified as the measurement region H.

Figure 2:
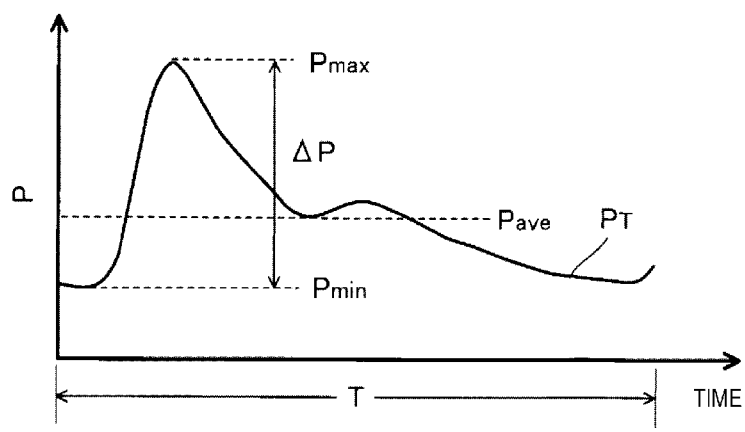
FIG. 2 is a graph illustrating a temporal change in a blood pressure.

FIG. 2 is a graph illustrating a temporal change PT in a blood pressure P. In the first embodiment, the systolic blood pressure (maximum blood pressure) Pmax and the diastolic blood pressure (minimum blood pressure) Pmin during an analysis period (about 0.5 to 1 second) T equivalent to one of beats are calculated. A sign ΔP in FIG. 2 denotes a pulse pressure during the analysis period T and a sign Pave is an average blood pressure during the analysis period T. The pulse pressure ΔP is a difference between the systolic blood pressure Pmax and the diastolic blood pressure Pmin. A time length of the analysis period T is not limited to one beat. For example, a period longer than a time length equivalent to one beat may be set as the analysis period T.

Here, knowledge that relations of Expressions (1) and (2) below are approximately established among the average blood pressure Pave, the pulse pressure ΔP, the systolic blood pressure Pmax, and the diastolic blood pressure Pmin can be obtained. Accordingly, the biological analysis device 100 according to the first embodiment calculates the pulse pressure ΔP and the average blood pressure Pave and calculates the systolic blood pressure Pmax and the diastolic blood pressure Pmin and from the pulse pressure ΔP and the average blood pressure Pave.

$$P_{max} = P_{ave} + \frac{2}{3}\Delta P \quad (1)$$

$$P_{min} = P_{ave} - \frac{1}{3}\Delta P \quad (2)$$

The biological analysis device 100 in FIG. 1 is mounted on the measurement region H (the upper arm or the wrist). The biological analysis device 100 according to the first embodiment is a wrist watch type portable device including a casing 12 and a belt 14. The biological analysis device 100 is mounted on the body of the subject by winding the belt 14 around the measurement region H.

Figure 3:
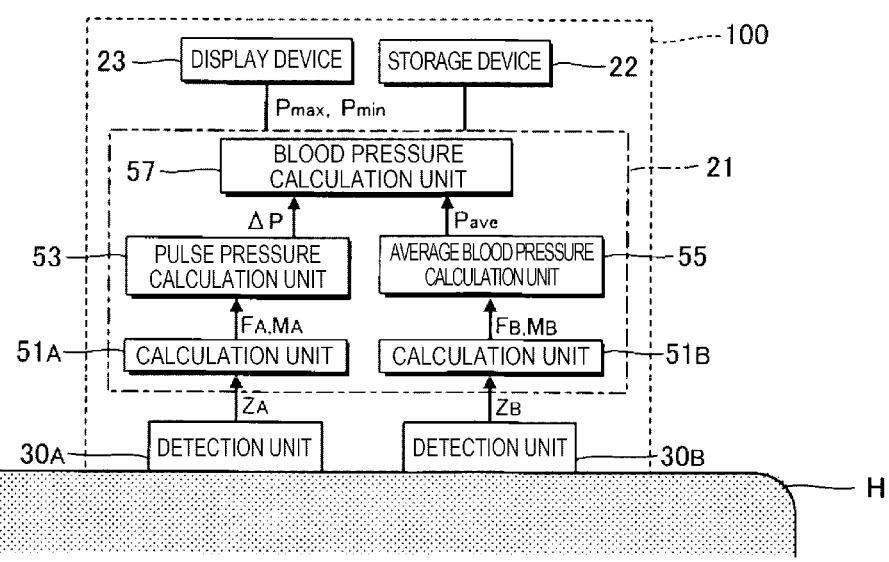

FIG. 3 is a diagram illustrating a configuration in which a function of the biological analysis device 100 is focused on. The biological analysis device 100 according to the first embodiment includes a control device 21, a storage device 22, a display device 23, a detection unit 30A, and a detection unit 30B. The control device 21 and the storage device 22 are installed inside the casing 12.

The display device 23 (for example, a liquid crystal panel) is installed on, for example, a surface of the casing 12 opposite to the measurement region H, as illustrated in FIG. 1. The display device 23 displays various images including a measurement result under the control of the control device 21.

Each detection unit 30 (30A and 30B) is a detection device that generates a detection signal Z in accordance with a state of the measurement region H. A detection signal ZA generated by the detection unit 30A is used in calculation of the pulse pressure ΔP. On the other hand, a detection signal ZB generated by the detection unit 30B is used in calculation of the average blood pressure Pave.

The control device 21 in FIG. 3 is an arithmetic processing device such as a central processing unit (CPU) or a field-programmable gate array (FPGA) and controls the whole biological analysis device 100. The storage device 22 is configured with, for example, a nonvolatile semiconductor memory and stores a program to be executed by the control device 21 and various kinds of data to be used by the control device 21. A configuration in which functions of the control device 21 are distributed to a plurality of integrated circuits can be adopted or a configuration in which some or all of the functions of the control device 21 are realized by a dedicated electronic circuit can also be adopted. In FIG. 3, the control device 21 and the storage device 22 are illustrated as separate elements, but the control device 21 containing the storage device 22 can also be realized by, for example, an application specific integrated circuit (ASIC) or the like.

The control device 21 according to the first embodiment realizes a plurality of functions (a calculation unit 51A, a calculation unit 51B, a pulse pressure calculation unit 53, an average blood pressure calculation unit 55, and a blood pressure calculation unit 57) of calculating the systolic blood pressure Pmax and the diastolic blood pressure Pmin by executing a program stored in the storage device 22. Some of the functions of the control device 21 may be realized by a dedicated electronic circuit.

In general, the pulse pressure calculation unit 53 calculates the pulse pressure ΔP using a predetermined index calculated from the detection signal ZA by the calculation unit 51A. On the other hand, the average blood pressure calculation unit 55 calculates the average blood pressure Pave using a predetermined index calculated from the detection signal ZB by the calculation unit 51B. The blood pressure calculation unit 57 calculates the systolic blood pressure Pmax and the diastolic blood pressure Pmin from the pulse pressure ΔP calculated by the pulse pressure calculation unit 53 and the average blood pressure Pave calculated by the average blood pressure calculation unit 55. As understood from the above-description, the detection unit 30A, the calculation unit 51A, and the pulse pressure calculation unit 53 are elements that calculates the pulse pressure ΔP, and the detection unit 30B, the calculation unit 51B, and the average blood pressure calculation unit 55 are element that calculates the average blood pressure Pave.

Pulse Pressure ΔP

Hereinafter, a process of calculating the pulse pressure ΔP will be described. Here, the blood pressure P is known to be expressed in Expression (3) that represents the following water-hammer. As understood from Expression (3), the blood pressure P is expressed as a product of blood density ρ, a pulse wave velocity PWV, and a blood flow rate V of a blood vessel.

$$P = \rho \times PWV \times V \quad (3)$$

Since a temporal change in the blood density ρ and the pulse wave velocity PWV is small, an amount of change of the blood density ρ and an amount of change of the pulse wave velocity PWV during the analysis period T can be considered to be constant. Accordingly, as expressed in Expression (4), the pulse pressure (that is, an amount of change of a pressure during the analysis period T) ΔP is expressed as a product of the blood density ρ, the pulse wave velocity PWV, and an amount of change (that is, an amplitude of a temporal change in the blood flow rate of a biological body) ΔV of the blood flow rate V during the analysis period T. The blood density ρ can be set to a predetermined value (for example, 1070 kg/m³) since an individual difference is small. That is, by calculating the pulse wave velocity PWV and an amplitude (hereinafter referred to as a "blood flow rate amplitude") ΔV of the blood flow rate V, it is possible to calculate the pulse pressure ΔP.

$$\Delta P = \rho \times PWV \times \Delta V \quad (4)$$

Figure 4:
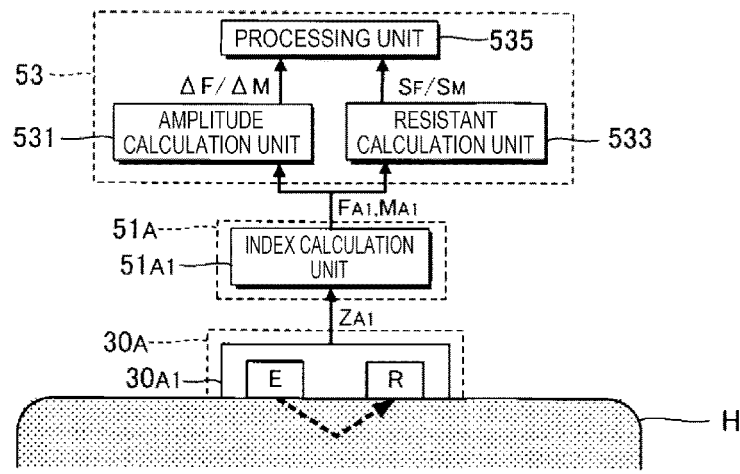
FIG. 4 is a diagram illustrating a configuration focusing on elements calculating a pulse pressure.

FIG. 4 is a diagram illustrating a configuration focusing on elements (the detection unit 30A, the calculation unit 51A, and the pulse pressure calculation unit 53) calculating the pulse pressure ΔP. The detection unit 30A according to the first embodiment includes a detection device 30A1 (an example of a first detection device). The detection device 30A1 is an optical sensor module that generates a detection signal ZA1 in accordance with a state of the measurement region H. Specifically, the detection device 30A1 includes a light-emitting unit E and a light-receiving unit R. The light-emitting unit E and the light-receiving unit R are installed at, for example, positions (generally, a surface in contact with the measurement region H) of the casing 12 facing the measurement region H.

The light-emitting unit E is a light source that radiates light to the measurement region H. The light-emitting unit E according to the first embodiment radiates a coherent laser beam to the measurement region H (biological body) with a narrowband. For example, a light-emitting element such as a vertical cavity surface emitting LASER (VCSEL) that emits a laser beam by resonance in a resonator is used appropriately as the light-emitting unit E. The light-emitting unit E according to the first embodiment radiates, for example, light with a predetermined wavelength (for example, 800 nm to 1300 nm) in a near infrared area to the measurement region H. The light-emitting unit E emits light under the control of the control device 21. The light emitted by the light-emitting unit E is not limited to the near infrared light.

Light incident on the measurement region H from the light-emitting unit E is repeatedly diffused and reflected while passing through the inside of the measurement region H to exit to the side of the casing 12. Specifically, the light passing through blood vessels inside the measurement region H and blood in the blood vessels exits from the measurement region H to the side of the casing 12.

The light-receiving unit R receives the laser beam reflected inside the measurement region H. Specifically, the light-receiving unit R generates a detection signal ZA1 indicating a light reception level of the light passing through the measurement region H. For example, a light-receiving element such as a photodiode (PD) that generates charges in accordance with the light reception intensity is used as the light-receiving unit R. Specifically, a light-receiving element in which a photoelectric conversion layer is formed of indium, gallium, and arsenic (InGaAs) having high sensitivity in a near infrared area is suitable as the light-receiving unit R. As understood from the above description, the detection device 30A1 according to the first embodiment is a reflective optical sensor in which the light-emitting unit E and the light-receiving unit R are located on side of the measurement region H. Here, a transmissive optical sensor in which the light-emitting unit E and the light-receiving unit R are located on opposite sides with the measurement region H interposed therebetween may be used as the detection device 30A1. The detection device 30A1 includes, for example, a driving circuit that drives the light-emitting unit E by applying a driving current and output circuits (for example, an amplification circuit and an A/D converter) that perform amplification and A/D conversion on a signal output by the light-receiving unit R, but these circuits are not illustrated in FIG. 4.

The light arriving at the light-receiving unit R includes a component diffused and reflected from a tissue (a stationary tissue) stationary inside the measurement region H and a component diffused and reflected from an object (generally, a red blood cell) moving inside a blood vessel inside the measurement region H. The frequency of light before and after the diffusion and reflection from a stationary tissue is not changed. However, before and after diffusion and reflection from a red blood cell, the frequency of light is changed by an amount of change (hereinafter referred to as a "frequency shift amount" proportional to a movement speed (that is, a blood flow rate) of the red blood cell. That is, the light passing through the measurement region H and arriving at the light-receiving unit R contains a component that is changed (frequency-shifted) by the frequency shift amount with respect to the frequency of the light emitting the light-emitting unit E. The detection signal ZA1 supplied to the control device 21 is an optical beat signal in which the frequency shift by a blood flow inside the measurement region H is reflected.

The calculation unit 51A according to the first embodiment includes an index calculation unit 51A1. The index calculation unit 51A1 calculates a blood mass index MA1 and a blood flow index FA1 of the measurement region H from the detection signal ZA1 generated by the detection device 30A1. The blood mass index MA1 (so-called MASS value) is an index related to a blood mass (specifically, the number of red blood cells in a unit volume) of a biological body. A blood mass is changed in conjunction with pulsation of a blood vessel diameter synchronized with a beat of a heart. That is, the blood mass index MA1 also correlates with a blood vessel diameter. Accordingly, the blood mass index MA1 can be paraphrased as an index of a blood vessel diameter (further, a unit area of a blood vessel) of a biological body. On the other hand, the blood flow index FA1 (so-called FLOW value) is an index related to a blood flow of a biological body (that is, a volume of blood moving in an artery in a unit time).

The index calculation unit 51A1 calculates an intensity spectrum from the detection signal ZA1 and calculates the blood mass index MA1 and the blood flow index FA1 from the intensity spectrum. The intensity spectrum is a distribution of an intensity (power or amplitude) G(f) of a signal component of the detection signal ZA1 at each frequency (Doppler frequency) on a frequency axis. In the calculation of the intensity spectrum, any known frequency analysis such as fast Fourier transform (FFT) can be adopted. The calculation of the intensity spectrum is executed repeatedly at a period shorter than the analysis period T.

The blood mass index M (MA1) is expressed in Expression (5a) below. A sign $\langle I^2 \rangle$ in Expression (5a) is an average intensity over the whole bandwidth of the detection signal ZA1 or an intensity G(0) (that is, an intensity of a direct-current component) at 0 Hz in the intensity spectrum.

$$M = \frac{\int_{f_L}^{f_H} G(f) df}{\langle I^2 \rangle} \tag{5a}$$

Figure 5:
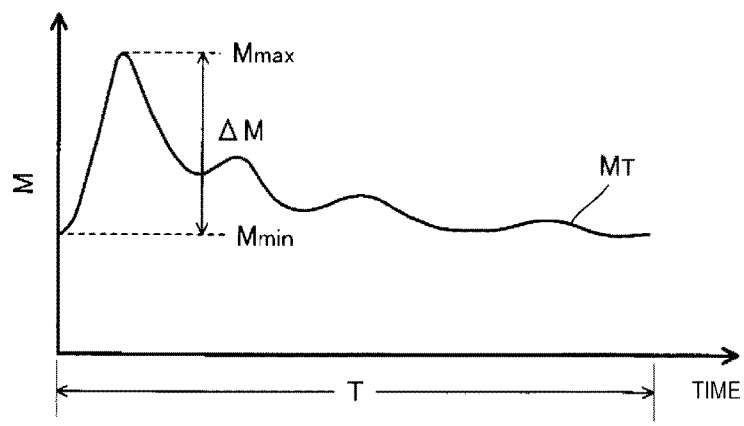
FIG. 5 is a graph illustrating a temporal change in a blood mass index.

As understood from Expression (5a), the blood mass index MA1 is calculated by integrating the intensity G(f) of each frequency f in the intensity spectrum in a range between a lower limit fL and upper limit fH on the frequency axis. The lower limit fL is less than the upper value fH. The blood mass index MA1 may be calculated by calculating Expression (5b) below in which an integral of Expression (5a) is replaced with a total sum (Σ). The sign Δf in Expression (5b) is a bandwidth corresponding to one intensity G(f) on the frequency axis and is equivalent to a horizontal width of each rectangle when the intensity spectrum is approximated with a plurality of rectangles arranged on the frequency axis. The calculation of the blood mass index MA1 is repeatedly executed at a period shorter than the analysis period T. FIG. 5 is a graph illustrating a temporal change MT in the blood mass index M (MA1) calculated during the analysis unit T by the index calculation unit 51A1. In addition to the blood mass index MA1 according to the first embodiment, blood mass indexes M (MB1, MA3, and MC) to be exemplified in each embodiment to be described below are also calculated as the blood mass index M of Expression (5a) or (5b). As understood from the above description, the blood mass index M is calculated (specifically, the intensity of each frequency in the intensity spectrum is integrated in a predetermined frequency range) from an intensity spectrum related to the frequency of light reflected and received inside in a biological body by radiating a laser beam.

$$M = \frac{\sum_{f=f_L}^{f_H} \Delta f \cdot G(f)}{\langle I^2 \rangle} \tag{5b}$$

The blood flow index F (FA1) is expressed in Expression (6a) below.

$$F = \frac{\int_{f_L}^{f_H} f \cdot G(f) df}{\langle I^2 \rangle} \tag{6a}$$

Figure 6:
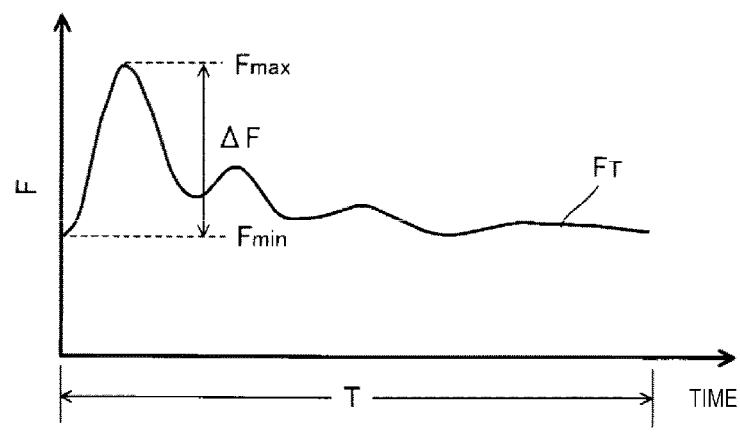
FIG. 6 is a graph illustrating a temporal change in a blood flow index.

As understood from Expression (6a), the blood flow index FA1 is calculated by integrating a product (f×G(f)) of the intensity G(f) of each frequency f in the intensity spectrum and the frequency f in a range between a lower limit fL and an upper limit fH on the frequency axis. Hereinafter, the product (f×G(f)) of the intensity G(f) of each frequency f in the intensity spectrum and the frequency f is referred to as a "frequency weighted intensity spectrum". The blood flow index FA1 may be calculated by calculating Expression (6b) below in which an integral of Expression (6a) is replaced with a total sum (Σ). The blood flow index FA1 is repeatedly calculated at a period shorter than the analysis period T. FIG. 6 is a graph illustrating a temporal change FT in the blood flow index F (FA1) calculated during the analysis unit T by the index calculation unit 51A1. In addition to the blood flow index FA1 according to the first embodiment, blood flow indexes F (FB1, FA3, and FC) to be exemplified in each embodiment to be described below are also calculated as the blood flow index F of Expression (6a) or (6b). As understood from the above description, the blood flow index F is calculated (specifically, the product of the intensity of each frequency in the intensity spectrum and the frequency is integrated in a predetermined frequency range) from an intensity spectrum related to the frequency of light reflected and received inside in a biological body by radiating a laser beam.

$$F = \frac{\sum_{f=f_L}^{f_H} f \cdot \Delta f \cdot G(f)}{\langle I^2 \rangle} \quad (6b)$$

The pulse pressure calculation unit 53 in FIG. 4 calculates the pulse pressure ΔP. Specifically, the pulse pressure calculation unit 53 calculates the pulse pressure ΔP of the measurement region H using the blood mass index MA1 and the blood flow index FA1 calculated by the index calculation unit 51A1. The pulse pressure calculation unit 53 according to the first embodiment includes an amplitude calculation unit 531, a resistance calculation unit 533, and a processing unit 535.

The amplitude calculation unit 531 calculates an index related to the blood flow amplitude ΔV (hereinafter referred to as an "amplitude index") using the blood mass index MA1 and the blood flow index FA1 generated by the index calculation unit 51A1. Specifically, the amplitude calculation unit 531 calculates an amplitude index in accordance with an amplitude ΔM of the temporal change MT in the blood mass index MA1 and an amplitude ΔF of the temporal change FT in the blood flow index F. As exemplified in FIG. 5, the amplitude ΔM is a difference between the maximum value Mmax and the minimum value Mmin of the blood mass index M (MA1) during the analysis period T. As exemplified in FIG. 6, the amplitude ΔF is a difference between the maximum value Fmax and the minimum value Fmin the blood flow index F (FA1) during the analysis period T.

Figure 7:
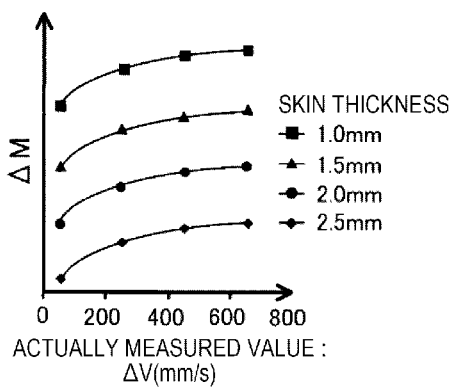
FIG. 7 is a graph illustrating a relation between a blood flow rate amplitude actually measured on a subject and an amplitude of a temporal change in a calculated blood mass index in a plurality of cases in which a skin thickness of the subject is changed.
Figure 8:
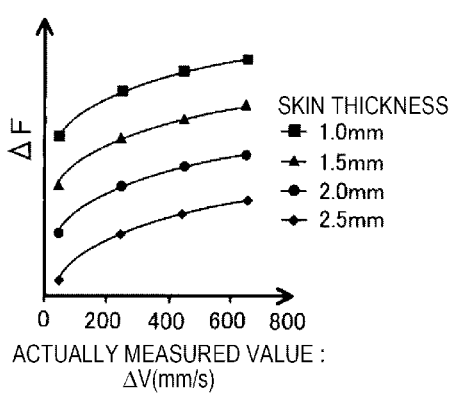
FIG. 8 is a graph illustrating a relation between a blood flow rate amplitude actually measured on a subject and an amplitude of a temporal change in a calculated blood flow index in a plurality of cases in which a skin thickness of the subject is changed.
Figure 9:
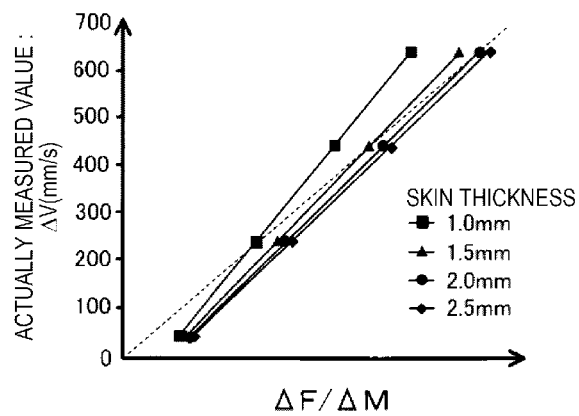
FIG. 9 is a graph illustrating a relation between a blood flow rate amplitude actually measured on a subject and a ratio of an amplitude of a temporal change in a blood mass index and an amplitude of a temporal change in the blood flow index in a plurality of cases in which a skin thickness of the subject is changed.

FIG. 7 is a graph illustrating a relation between the blood flow rate amplitude ΔV actually measured on the subject and the amplitude ΔM specified by the index calculation unit 51A1. FIG. 8 is a graph illustrating a relation between the blood flow rate amplitude ΔV actually measured on the subject and the amplitude ΔF specified by the index calculation unit 51A1. FIGS. 7 and 8 illustrate a plurality of cases in which a skin thickness of the subject is changed. The skin thickness is a distance between the surface of the skin and a blood vessel. The blood flow rate amplitude ΔV is an actually measured value by a known measurement technology. As ascertained from FIGS. 7 and 8, each of the amplitude ΔM and the amplitude ΔF correlates with the blood flow amplitude ΔV and is considerably changed in accordance with a skin thickness. FIG. 9 is a graph illustrating a relation between the blood flow rate amplitude ΔV actually measured on the subject and a ratio of the amplitude ΔM and the amplitude ΔF specified by the index calculation unit 51A1 (specifically, a ratio of the amplitude ΔF to the amplitude ΔM) in the plurality of cases in which the skin thickness of the subject is changed. As ascertained from FIG. 9, it is possible to obtain the knowledge that the ratio (ΔF/ΔM) of the amplitude ΔF to the amplitude ΔM positively correlates with the blood flow rate amplitude ΔV (when one of the amplitudes increases, the other also increases) and a change in accordance with the skin thickness is small. As a background of the foregoing knowledge, the amplitude calculation unit 531 according to the first embodiment calculates the ratio (ΔF/ΔM) of the amplitude ΔF to the amplitude ΔM as an amplitude index.

The resistance calculation unit 533 in FIG. 4 calculates an index related to the pulse wave velocity PWV using the blood mass index MA1 and the blood flow index FA1 generated by the index calculation unit 51A1. The pulse wave velocity PWV correlates with blood vessel resistance. Specifically, when the blood vessel resistance is high, the pulse wave velocity PWV tends to be faster. On the basis of this tendency, an index related to the pulse wave velocity PWV is referred to as a "resistance index". That is, the resistance calculation unit 533 calculates a resistance index using the blood mass index MA1 and the blood flow index FA1. Specifically, the resistance index is calculated in accordance with a value (hereinafter referred to as a "blood mass integration value") SM obtained by integrating the blood mass index MA1 during an integration period and a value (hereinafter referred to as a "blood flow integration value") SF obtained by integrating the blood flow index FA1 during the integration period. For example, the integration period is identical to the analysis period T (that is, a period equivalent to one of beats). The integration period may be different from the analysis period T.

In the first embodiment, the resistance index is calculated in accordance with the blood mass integration value SM obtained by integrating a normalized blood mass index MN during the analysis period T and the blood flow integration value SF obtained by integrating the normalized blood flow index FN during the analysis period T. The normalized blood mass index MN is a numerical value obtained by normalizing the blood mass index MA1 within a normalization range, and the normalized blood flow index FN is a numerical value obtained by normalizing the blood flow index FA1 within the normalization range.

Figure 10:
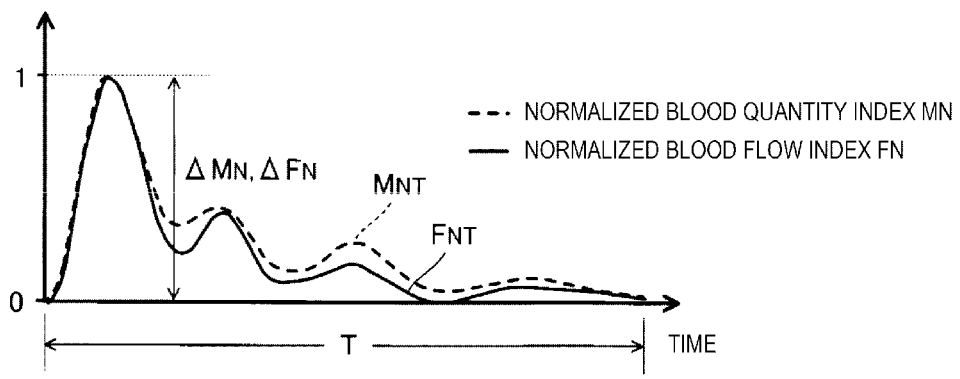
FIG. 10 is a graph illustrating a temporal change in a normalized blood quality index and a temporal change in a normalized blood flow index.

FIG. 10 is a graph illustrating a temporal change MNT in a normalized blood quality index MN and a temporal change FNT in a normalized blood flow index FN. FIG. 10 illustrates a case in which each of the blood mass index (blood quantity index) MA1 and the blood flow index FA1 is normalized in a normalization range equal to or greater than 0 and equal to or less than 1. That is, the blood mass index MA1 and the blood flow index FA1 are normalized so that the minimum value Mmin and the minimum value Fmin during the analysis period T are 0 and the maximum value Mmax and the maximum value Fmax during the analysis period T are 1. That is, the amplitude ΔMN of the normalized blood mass index MN and the amplitude ΔFN of the normalized blood flow index FN are 1. Specifically, the blood mass integration value SM is a temporal integration value of the normalized blood mass index MN during the analysis period T, and the blood flow integration value SF is a temporal integration value of the normalized blood flow index FN during the analysis period T. The area of a region surrounded by a curve line representing a temporal change MNT of the normalized blood mass index MN and a time axis (a straight line of MN=0) is the blood mass integration value SM, and the area of a region surrounded by a curve line representing a temporal change FNT of the normalized blood flow index FN and a time axis (a straight line of FN=0) is the blood flow integration value SF.

Figure 11:
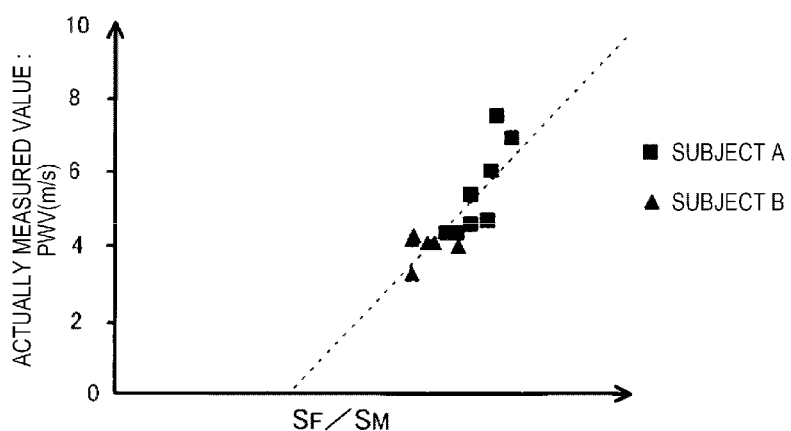
FIG. 11 is a graph illustrating a relation between a pulse wave velocity actually measured on a plurality of subjects and a ratio of a blood mass integration value and a blood flow integration value in the subjects.

FIG. 11 is a graph illustrating a relation between the pulse wave velocity PWV actually measured on a plurality of subjects and a ratio of the blood mass integration value SM and the blood flow integration value SF on subjects. The pulse wave velocity PWV is an actually measured value by a known measurement technology. As ascertained from FIG. 11, it is possible to obtain the knowledge that the pulse wave velocity PWV correlates with the ratio of the blood mass integration value SM and the blood flow integration value SF (specifically, a ratio of the blood flow integration value SF to the blood mass integration value SM). As a background of the foregoing knowledge, the resistance calculation unit 533 according to the first embodiment calculates the ratio (SF/SM) of the blood mass integration value SM and the blood flow integration value SF as a resistance index.

Figure 12:
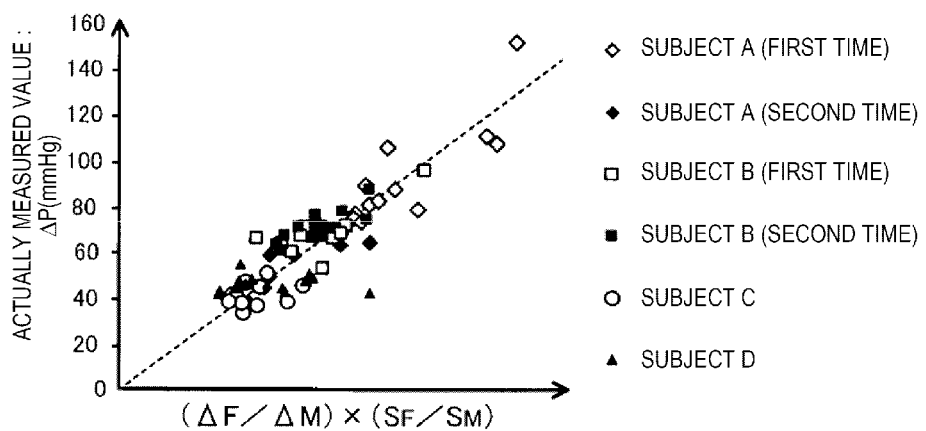
FIG. 12 is a graph illustrating a relation between a pulse pressure actually measured on a subject and a plurality of product of an amplitude index and a resistance index on the subjects.

The processing unit 535 in FIG. 4 calculates the pulse pressure ΔP in accordance with the amplitude index calculated by the amplitude calculation unit 531 and the resistance index calculated by the resistance calculation unit 533. Specifically, the processing unit 535 calculates the pulse pressure ΔP in accordance with the product of the amplitude index and the resistance index using Expression (4) described above. FIG. 12 is a graph illustrating a relation between the pulse pressure ΔP actually measured on a plurality of subject and a product of the amplitude index (ΔF/ΔM) and a resistance index (SF/SM) on the subjects. The pulse pressure ΔP is an actually measured value by a known measurement technology. As ascertained from FIG. 12, the product ((ΔF/ΔM)×(SF/SM)) of the amplitude index and the resistance index correlates with (specifically, has a proportional relation with) the pulse pressure ΔP. Accordingly, the pulse pressure ΔP is expressed in Expression (7) below. As understood from Expression (7), the pulse pressure ΔP can be calculated by multiplying the product of the amplitude index and the resistance index by a predetermined coefficient K. For example, the coefficient K is set in accordance with an attribute (for example, age, sex, and weight) of the subject. As understood from the above-description, the pulse pressure calculation unit 53 functions as an element that calculates the pulse pressure ΔP in accordance with the blood mass integration value SM and the blood flow integration value SF.

$$\Delta P = K \times \frac{SF}{SM} \times \frac{\Delta F}{\Delta M} \quad (7)$$

As described above, in the first embodiment, the amplitude index (ΔF/ΔM) is calculated in accordance with the amplitude ΔM of the temporal change MT in the blood mass index MA1 and the amplitude ΔF of the temporal change FT in the blood flow index FA1, the resistance index (SF/SM) is calculated in accordance with the blood mass integration value SM and the blood flow integration value SF, and the pulse pressure ΔP is calculated from the amplitude index and the resistance index. In each calculation of the foregoing indexes (the amplitude index, the resistance index, and the pulse pressure ΔP), a cuff is unnecessary in principle. Accordingly, it is possible to calculate the pulse pressure ΔP with high precision while reducing a physical load of a subject.

In the first embodiment, in particular, it is possible to calculate the pulse pressure ΔP with high precision using the tendency of the correlation of the product of the ratio (ΔF/ΔM) of the amplitude ΔM and the amplitude ΔF and the ratio (SF/SM) of the blood mass integration value SM and the blood flow integration value SF with the pulse pressure ΔP. Further, by taking the ratio of the amplitude ΔM of the blood mass index MA1 and the amplitude ΔF of the blood flow index FA1, it is possible to calculate an amplitude index with high precision even when a skin thickness is changed.

Average Blood Pressure Pave

Figure 13:
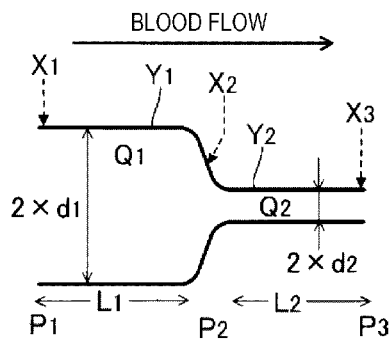
FIG. 13 is a schematic diagram illustrating a blood vessel of an arm.

Hereinafter, a process of calculating the average blood pressure Pave will be described. FIG. 13 is a schematic diagram illustrating a blood vessel of an arm. FIG. 13 illustrates an artery (for example, a radial artery) Y1 and an arteriole (for example, a finger artery) Y2 connected to the artery Y1. As exemplified in FIG. 3, a site X1 is a predetermined site in the artery Y1, a site X2 is a site between the artery Y1 and an arteriole Y2, and a site X3 is a site of an erasure of the arteriole Y2. That is, the site X1 is closer to a heart than the site X3.

A relation among a blood pressure P1 at the site X1 in the artery Y1, a blood pressure P2 at the site X2 between the artery Y1 and the arteriole Y2, and a blood pressure P3 at the site X3 of the erasure of the arteriole Y2 is expressed in Expressions (8) and (9) below using the Hagen-Poiseuille law. A sign L1 in Expression (8) is the length of the artery Y1, a sign Q1 is a blood flow of the artery Y1, and a sign d1 is a blood vessel diameter (radius) of the artery Y1. A sign L2 in Expression (9) is the length of the arteriole Y2, a sign Q2 is a blood flow of the arteriole Y2, and a sign d2 is a blood vessel diameter (radius) of the arteriole Y2. A sign ρ in Expressions (8) and (9) is blood density.

$$P_1 - P_2 = \frac{8\rho L_1 Q_1}{\pi d_1^4} \quad (8)$$

$$P_2 - P_3 = \frac{8\rho L_2 Q_2}{\pi d_2^4} \quad (9)$$

An amount of change (that is, P1−P3) of a blood pressure from the site X1 to the site X3 is expressed in Expression (10) below using Expressions (8) and (9).

$$P_1 - P_3 = \frac{8\rho L_1 Q_1}{\pi d_1^4} + \frac{8\rho L_2 Q_2}{\pi d_2^4} \quad (10)$$

Figure 14:
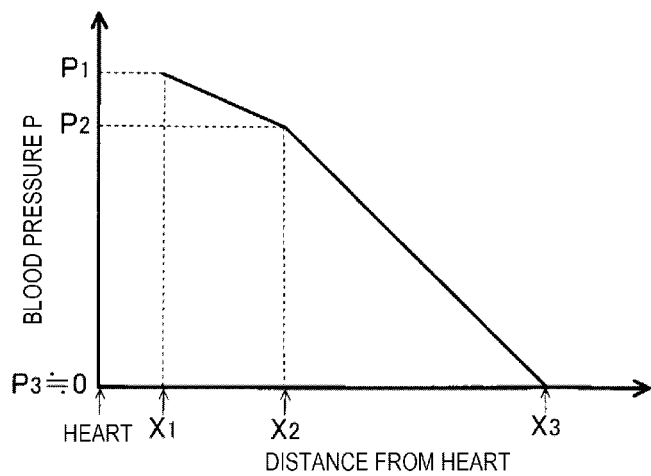
FIG. 14 is a graph illustrating a relation between a distance from a heart to a specific part on a blood vessel and an average blood pressure of the specific part.

FIG. 14 is a graph illustrating a relation between a distance from a heart to a specific part on a blood vessel and an average blood pressure of the specific part. As understood from FIG. 14, the amount of change (that is, P1−P2) of the blood pressure from the site X1 to the site X2 tends to be sufficiently smaller than an amount of change (that is, P2−P3) of a blood pressure from the site X2 to the site X3. Specifically, the amount of change (P1−P2) is about 1 to 5 mmHg and the amount of change (P2−P3) is about 100 mmHg. The blood pressure P3 at the site X3 of the erasure of the arteriole Y2 is known to be very small (for example, a few mmHg). Accordingly, when the blood pressure P3 of the amount of change (P1−P2) is assumed to be 0 mmHg, Expression (11) below is derived from Expression (10). As understood from Expression (11), the blood pressure P1 is approximate to the amount of change (P1−P3).

$$P_1 - P_3 \approx P_1 = \frac{8\rho L_2 Q_2}{\pi d_2^4} \quad (11)$$

Since an individual difference in the blood density ρ is small, the blood density ρ can be set to a predetermined value (for example, 1070 kg/m³). The distance L2 can be set to a predetermined value estimated from a height, a sex, and the like of a subject. That is, by calculating a blood flow Q2 and a blood vessel diameter d2 of the arteriole Y2, the blood pressure P1 of the artery Y1 can be calculated. Accordingly, according to the first embodiment, the average blood pressure Pave is calculated using Expression (11).

Figure 15:
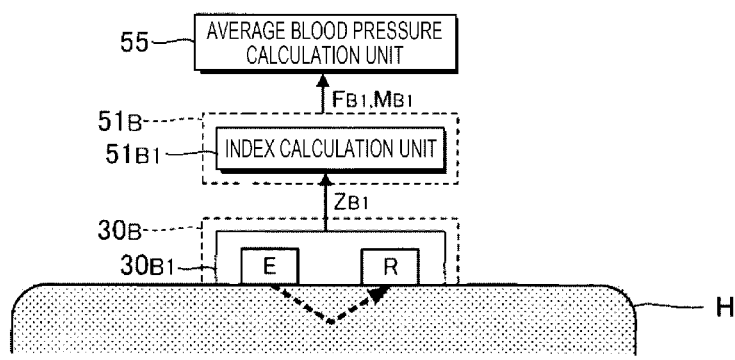

FIG. 15 is a diagram illustrating a configuration in which elements (the detection unit 30B, the calculation unit 51B, and the average blood pressure calculation unit 55) calculating the average blood pressure Pave are focused on. The detection unit 30B according to the first embodiment includes a detection device 30B1 (an example of a second detection device). The detection device 30B1 is an optical sensor module that generates a detection signal ZB1 in accordance with a state of the measurement region H. The detection device 30B1 includes a light-emitting unit E and a light-receiving unit R similar to those of the detection device 30A1 in FIG. 4. The light-emitting unit E and the light-receiving unit R are installed, for example, at positions of the casing 12 facing the measurement region H (generally, a surface in contact with the measurement region H).

The calculation unit 51B in FIG. 15 includes an index calculation unit 51B1. The index calculation unit 51B1 calculates a blood vessel diameter index and a blood flow index FB1 of the measurement region H. The blood vessel diameter index is an index related to a blood vessel diameter (and a cross-sectional area of a blood vessel) of a biological body. As described above, the blood vessel diameter index correlates with the blood mass index M. Accordingly, according to the first embodiment, the blood mass index M is exemplified as a blood vessel diameter index. Specifically, the index calculation unit 51B1 calculates the blood mass index MB1 and the blood flow index FB1 of the measurement region H from the detection signal ZB1 generated by the detection device 30B1. The blood mass index MB1 is calculated from Expression (5a) or (5b) described above and the blood flow index FB1 is calculated from Expression (6a) or (6b) described above.

The average blood pressure calculation unit 55 calculates the average blood pressure Pave of the biological body. Specifically, the average blood pressure calculation unit 55 calculates the average blood pressure Pave of the biological body in accordance with the blood mass index MB1 and the blood flow index FB1 calculated by the index calculation unit 51B1. The average blood pressure calculation unit 55 according to the first embodiment calculates the average blood pressure Pave in accordance with an average value Mave obtained by averaging the blood mass indexes MB1 during the analysis period T and an average value Fave obtained by averaging the blood flow indexes FB1 during the analysis period T. The average value Mave is an average (for example, a simple average or a weighted average) of the plurality of blood mass indexes MB1 calculated during the analysis period T. The average value Fave is an average (for example, a simple average or a weighted average) of the plurality of blood flow indexes FB1 calculated during the analysis period T.

As described above, the blood mass index M correlates with a blood vessel diameter d. Specifically, a cubic root ($M^{1/3}$) of the blood mass index M is equivalent to the blood vessel diameter d. The third power of the blood vessel diameter d2 is paraphrased to be equivalent to the blood mass index M. The blood flow index F is equivalent to a blood flow Q. In consideration of the foregoing relation, Expression (11) described above is modified into Expression (12) below.

$$P_{ave} = K \times \frac{F_{ave}}{M_{ave}^{4/3}} \quad (12)$$

The average blood pressure calculation unit 55 according to the first embodiment calculates the average blood pressure Pave by calculation of Expression (12). A sign K is a coefficient determined in advance in accordance with the blood density ρ, a length L2 of an arteriole, and the like. As understood from Expression (12), the average blood pressure Pave is calculated in accordance with $F_{ave}/M_{ave}^{4/3}$. The coefficient K is set from an actually measured value of the average blood pressure Pave actually measured, for example, using a cuff or the like and a calculated value of $F_{ave}/M_{ave}^{4/3}$ of Expression (12) (for example, K=actually measured value/calculated value).

As described above, according to the first embodiment, the average blood pressure Pave is calculated in accordance with the blood vessel diameter index (the blood mass index MB1) and the blood flow index FB1. Here, for example, in a configuration in which a biological body is compressed in calculation of an average blood pressure (for example, a configuration in which an average blood pressure is calculated using a cuff or the like), an error caused due to a difference in a pressure force can occur. However, according to the first embodiment, since the average blood pressure Pave is calculated in accordance with the blood vessel diameter index (the blood mass index MB1) and the blood flow index FB1, it is unnecessary to compress a biological body. Furthermore, an error caused due to a difference in a pressure force can be reduced and the average blood pressure Pave can be calculated with high precision.

Incidentally, in calculation of the blood flow index FB1, a blood flow rate sensor that radiates an ultrasonic wave to a biological body can also be used. However, when an ultrasonic wave radiation type of blood flow rate sensor is used, a skin thickness of a measurement region or the flow index FB1 has an influence on a condition that a radiation surface of an ultrasonic wave comes into contact with a biological body (the degree or a pressure of adherence). It is difficult to actually specify an index related to a blood pressure (for example, an average blood pressure) with high precision. When the ultrasonic wave radiation type of blood flow rate sensor is used, there is also the problem that the size of a biological analysis device increases. According to the first embodiment, however, since a laser beam is used in calculation of the blood flow index FB1, the influence of a skin thickness or the like can be reduced and the average blood pressure Pave can be measured with higher precision than in a case in which an ultrasonic wave radiation type blood flow rate sensor is used. It is possible to miniaturize the biological analysis device 100.

Systolic Blood Pressure Pmax and Diastolic Blood Pressure Pmin

Hereinafter, a process of calculating the systolic blood pressure Pmax and the diastolic blood pressure Pmin will be described. The blood pressure calculation unit 57 in FIG. 3 calculates the systolic blood pressure Pmax and the diastolic blood pressure Pmin in accordance with the pulse pressure ΔP calculated by the pulse pressure calculation unit 53 and the average blood pressure Pave calculated by the average blood pressure calculation unit 55. Specifically, the blood pressure calculation unit 57 calculates the systolic blood pressure Pmax by Expression (1) described above and calculates the diastolic blood pressure Pmin by Expression (2) described above. The control device 21 causes the display device 23 to display the systolic blood pressure Pmax and the diastolic blood pressure Pmin calculated by the blood pressure calculation unit 57.

FIG. 16 is a flowchart illustrating a process (hereinafter referred to as a "biological analysis process") executed by the control device 21. The biological analysis process in FIG. 16 is executed during each analysis period T on the time axis. When the biological analysis process starts, the control device 21 calculates the pulse pressure ΔP (Sa1). Subsequently, the control device 21 calculates the average blood pressure Pave (Sa2). Then, the control device 21 (the blood pressure calculation unit 57) calculates the systolic blood pressure Pmax and the diastolic blood pressure Pmin in accordance with the calculated pulse pressure ΔP and average blood pressure Pave (Sa3). In the calculation of the blood pressure P, Expressions (1) and (2) described above are used. The control device 21 causes the display device 23 to display the calculated systolic blood pressure Pmax and diastolic blood pressure Pmin (Sa4). The order of the calculation (Sa1) of the pulse pressure ΔP and the calculation (Sa2) of the average blood pressure Pave may be reversed. By executing the above-described biological analysis process during each analysis period T, a time series of the systolic blood pressure Pmax (that is, a temporal change in the systolic blood pressure Pmax) and a time series of the diastolic blood pressure Pmin (a temporal change in the diastolic blood pressure Pmin) are calculated.

FIG. 17 is a flowchart illustrating specific content of a process Sa1 of calculating the pulse pressure ΔP. The index calculation unit 51A1 generates the temporal change MT in the blood mass index (blood quantity index) MA1 during the analysis period T (Sa11). In the calculation of the blood mass index MA1, Expression (5a) or (5b) described above is used. Subsequently, the index calculation unit 51A1 generates the temporal change FT in the blood flow index FA1 during the analysis period T (Sa12). In the calculation of the blood flow index FA1, Expression (6a) or (6b) described above is used.

The amplitude calculation unit 531 calculates the amplitude index in accordance with the amplitude ΔM of the temporal change MT and the amplitude ΔF of the temporal change FT generated by the index calculation unit 51A1 (Sa13). Specifically, the ratio (ΔF/ΔM) of the amplitude ΔM and the amplitude ΔF is calculated as the amplitude index. Subsequently, the resistance calculation unit 533 calculates the resistance index from the temporal change MT and the temporal change FT generated by the index calculation unit 51A1 (Sa14). Specifically, the ratio (SF/SM) of the blood mass integration value SM and the blood flow integration value SF is calculated as the resistance index. The processing unit 535 calculates the pulse pressure ΔP in accordance with the amplitude index calculated by the amplitude calculation unit 531 and the resistance index calculated by the resistance calculation unit 533 (Sa15). In the calculation of the pulse pressure ΔP, Expression (7) described above is used. That is, the pulse pressure ΔP in accordance with the product of the amplitude index and the resistance index is calculated. The order of the generation (Sa11) of the temporal change MT in the blood mass index MA1 and the generation (Sa12) of the temporal change FT in the blood flow index FA1 may be reversed. The order of the process (Sa13) of calculating the amplitude index and the process (Sa14) of calculating the resistance index may be reversed.

Figure 18:
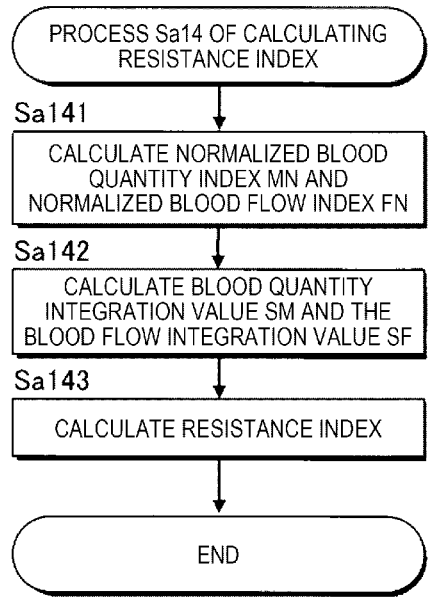
FIG. 18 is a flowchart illustrating specific content of a process of calculating a resistance index.

FIG. 18 is a flowchart illustrating specific content of a process Sa14 of calculating the resistance index. The resistance calculation unit 533 calculates the normalized blood mass index (normalized blood quantity index) MN and the normalized blood flow index FN respectively obtained by normalizing the blood mass index (blood quantity index) MA and the blood flow index FA within a normalization range (Sa141). Subsequently, the resistance calculation unit 533 calculates the blood mass integration value SM and the blood flow integration value SF respectively obtained by integrating the normalized blood mass index MN and the normalized blood flow index FN during the analysis period T (Sa142). The resistance calculation unit 533 calculates the ratio (SF/SM) of the blood mass integration value SM and the blood flow integration value SF as the resistance index (Sa143).

Figure 19:
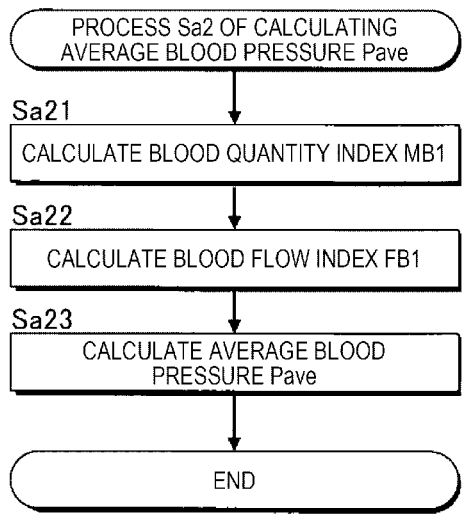
FIG. 19 is a flowchart illustrating specific content of a process of calculating an average blood pressure.

FIG. 19 is a flowchart illustrating specific content of a process Sa2 of calculating the average blood pressure Pave. The index calculation unit 51B1 calculates the blood mass index (blood quantity index) MB1 at each of a plurality of time points within the analysis period T (Sa21). In the calculation of the blood mass index MB1, Expression (5a) or (5b) described above is used. Subsequently, the index calculation unit 51B1 calculates the blood flow index FB1 at each of a plurality of time points within the analysis period T (Sa22). In the calculation of the blood flow index FB1, Expression (6a) or (6b) described above is used. The average blood pressure calculation unit 55 calculates the average blood pressure Pave in accordance with the blood mass index MB1 and the blood flow index FB1 calculated by the index calculation unit 51B1 (Sa23). The order of the calculation (Sa21) of the blood mass index MB1 and the calculation (Sa22) of the blood flow index FB1 may be reversed.

Figure 20:
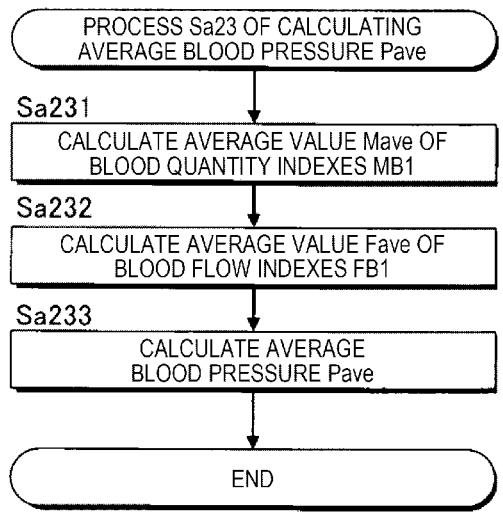
FIG. 20 is a flowchart illustrating specific content of a process of calculating an average blood pressure.

FIG. 20 is a flowchart illustrating specific content of the process Sa23 of calculating the average blood pressure Pave. The average blood pressure calculation unit 55 calculates the average value Mave obtained by averaging the blood mass indexes (blood quantity index) MB1 during the analysis period T (Sa231). The average blood pressure calculation unit 55 calculates the average value Fave obtained by averaging the blood flow indexes FB1 during the analysis period T (Sa232). Then, the average blood pressure calculation unit 55 calculates the average blood pressure Pave in accordance with the average value Mave and the average value Fave (Sa233). In the calculation of the average blood pressure Pave, Expression (12) described above is used. That is, the average blood pressure Pave is calculated in accordance with Fave/Mave$^{4/3}$. The order of the calculation (Sa231) of the average value Mave and the calculation (Sa232) of the average value Fave may be reversed.

As described above, according to the first embodiment, since the systolic blood pressure Pmax and the diastolic blood pressure Pmin are calculated in accordance with the pulse pressure ΔP and the average blood pressure Pave, the systolic blood pressure Pmax and the diastolic blood pressure Pmin can be calculated with higher precision than, for example, in the configuration in which the systolic blood pressure Pmax and the diastolic blood pressure Pmin are calculated using a maximum value or a minimum value of a blood vessel diameter.

Blood Vessel of Measurement Region H

Figure 21:
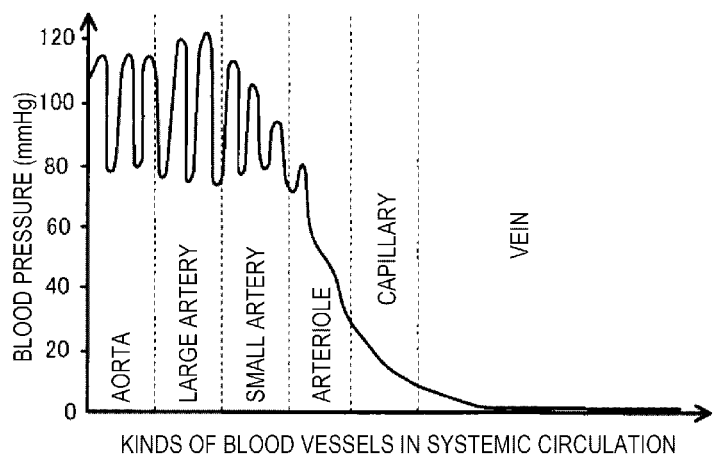
FIG. 21 is a graph illustrating a relation between blood pressures and kinds of blood vessels in a systemic circulation.

FIG. 21 is a graph illustrating a relation between blood pressures and kinds of blood vessels in a systemic circulation. As described above, a difference between the systolic blood pressure Pmax and the diastolic blood pressure Pmin is the pulse pressure ΔP. Accordingly, by using a blood vessel in which the difference between the systolic blood pressure Pmax and the diastolic blood pressure Pmin is large to calculate the pulse pressure ΔP, it is possible to calculate the pulse pressure ΔP with higher precision. As ascertained from FIG. 21, larger pulsation appears in a blood pressure of an artery (a large artery and a small artery) than in other blood vessels. Accordingly, in the calculation of the pulse pressure ΔP, it is preferable to use the detection signal ZA in which a state of an artery (for example, a brachial artery, a radial artery, or an ulnar artery) inside the measurement region H is reflected. The detection signal ZA in which a state of an arteriole is reflected may be used in the calculation of the pulse pressure ΔP.

As understood from Expression (11), a blood pressure P1 is approximate to the amount of change (P1−P3). That is, the average blood pressure Pave can be calculated with higher precision by using a blood vessel for which a slope (gradient) of a change in a blood pressure in a blood vessel is large in the calculation of the average blood pressure Pave. As ascertained from FIG. 21, the slope of the pressure of an arteriole is greater than that of the other blood vessels. Accordingly, in the calculation of the average blood pressure Pave, it is preferable to use the detection signal ZB in which a state of an arteriole inside the measurement region H is reflected.

As a background of the foregoing knowledge, in the first embodiment, the detection device 30A1 generating the detection signal ZA1 is installed at a position facing an artery (with a diameter of 2 mm to 5 mm) inside the measurement region H. On the other hand, the detection device 30B1 generating the detection signal ZB1 is installed at a position facing an arteriole (with a diameter of 0.02 mm to 2 mm) inside the measurement region H. When a wrist is the measurement region H, for example, the detection device 30A1 is installed at a position close to a radial artery or an ulnar artery in the palm of the wrist and the detection device 30B1 is installed on the back of the wrist. When an upper arm is the measurement region H, for example, the detection device 30A1 is installed at a position close to a brachial artery inside the upper arm and the detection device 30B1 is installed on the outside of the upper arm. For example, as understood from the above description in which the detection device 30A1 is installed on a surface of a trunk in the upper arm and the detection device 30B1 is installed on the opposite surface to the trunk, the detection device 30A1 and the detection device 30B1 are installed at positions in the circumferential direction of a limb (for example, an upper arm or a wrist) of a biological body.

In the configuration in which the detection device 30A1 and the detection device 30B1 are provided at the positions in the circumferential direction of the limb of the biological body, it is possible to obtain the advantage that it is possible to generate two detection signals Z in which states of two blood vessels (for example, an artery and an arteriole) different at approximate positions in the biological body are reflected. However, the positions at which the two detection devices (30A1 and 30B1) are disposed are not limited to the circumferential direction of the biological body. For example, the detection devices (30A1 and 30B1) may be disposed on ears, temples, a trunk, or the like. For example, a configuration in which the detection device 30A1 is disposed on one of the ears or the temples and the detection device 30B1 is disposed on the other can be adopted or a configuration in which the detection device 30A1 is disposed on one of the ears or inner ears and the detection device 30B1 is disposed on the other can be adopted. In the calculation of the pulse pressure ΔP, the detection signal ZB1 obtained from an arteriole may be used.

Modification Examples of First Embodiment

The elements (the detection unit 30A, the calculation unit 51A, and the pulse pressure calculation unit 53) that calculate the pulse pressure ΔP are not limited to the configuration exemplified in FIG. 4.

Modification Example 1

Figure 22:
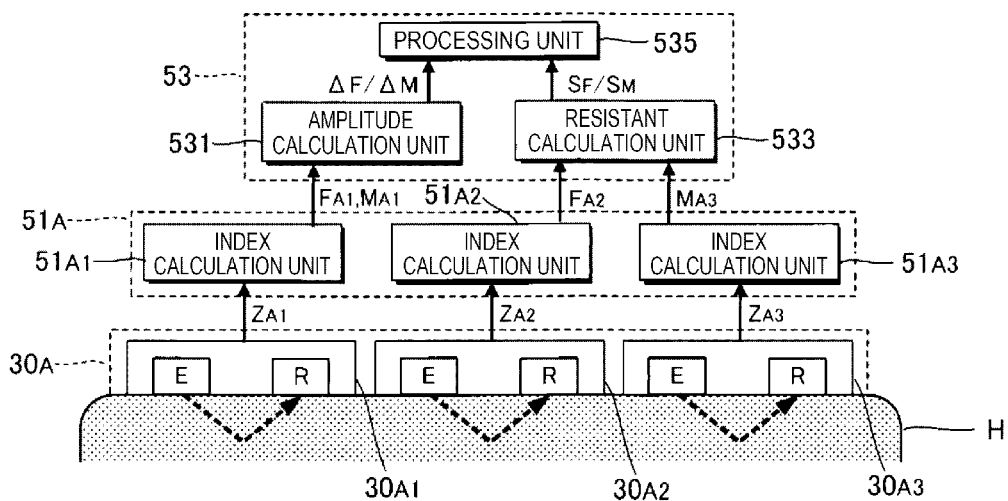
FIG. 22 is a diagram illustrating a configuration in which elements calculating a pulse pressure are focused on according to a modification example of the first embodiment.

FIG. 22 is a diagram illustrating a configuration in which elements calculating the pulse pressure ΔP are focused on according to a modification example (Modification Example 1) of the first embodiment. In the first embodiment, the amplitude index and the resistance index have been calculated using the detection signal ZA1 generated by the detection device 30A1. In Modification Example 1, however, the amplitude index is calculated using the detection signal ZA1 generated by the detection device 30A1 and the resistance index is calculated using detection signals ZA (ZA2 and ZA3) generated by two detection devices 30A (30A2 and 30A3) different from the detection device 30A1.

The detection unit 30A according to Modification Example 1 includes the detection device 30A2 and the detection device 30A3 in addition to the detection device 30A1 similar to that of the first embodiment. The detection device 30A1 according to Modification Example 1 has a configuration and a function similar to those of the first embodiment and generates a detection signal ZA1 in accordance with a state of the measurement region H. The detection device 30A2 includes a light-emitting unit R and a light-receiving unit E similar to those of the detection device 30A1 and generates a detection signal ZA2 in accordance with a state of the measurement region H. Similarly, the detection device 30A3 includes a light-emitting unit R and a light-receiving unit E and generates a detection signal ZA3 in accordance with a state of the measurement region H. As the light-emitting unit E of the detection device 30A3, a light-emitting element such as a light-emitting diode (LED) radiating incoherent light to the measurement region H is appropriately used. A VCSEL emitting a coherent laser beam may be used as the light-emitting unit E. The light-receiving unit R of the detection device 30A3 generates the detection signal ZA3 in accordance with a light reception level of light passing through the inside of the measurement region H like the light-receiving unit R of the detection device 30A2. The detection signal ZA3 is a signal indicating a photoelectric volume pulse wave. A pressure sensor that generates a detection signal indicating displacement of the surface of the measurement region H (that is, indicating displacement of a blood vessel diameter) may be adopted as the detection device 30A3.

The calculation unit 51A according to Modification Example 1 includes an index calculation unit 51A2 and an index calculation unit 51A3 in addition to an index calculation unit 51A1 similar to that of the first embodiment. The index calculation unit 51A1 according to Modification Example 1 calculates a blood mass index MA1 and a blood flow index FA1 of the measurement region H from the detection signal ZA1 generated by the detection device 30A1 as in the first embodiment.

The index calculation unit 51A2 calculates a blood flow index FA2 from the detection signal ZA2 generated by the detection device 30A2. The blood flow index FA2 is calculated in a scheme similar to the blood flow index FA1 (Expression (6a) or (6b)). The index calculation unit 51A3 calculates a blood mass index MA3 from the detection signal ZA3 generated by the detection device 30A3. As described above, the blood mass index MA3 correlates with a blood vessel diameter. On the assumption of the foregoing relation, the index calculation unit 51A3 calculates displacement of a blood vessel diameter from the detection signal ZA3 and calculates the blood mass index MA3 from the displacement of the blood vessel diameter.

The pulse pressure calculation unit 53 according to Modification Example 1 includes the amplitude calculation unit 531, the resistance calculation unit 533, and the processing unit 535 as in the first embodiment. The amplitude calculation unit 531 calculates the amplitude index ($\Delta F/\Delta M$) of the blood mass index MA1 and the blood flow index FA1 calculated by the index calculation unit 51A1 as in the first embodiment. The resistance calculation unit 533 according to Modification Example 1 calculates the resistance index (SF/SM) from the blood flow index FA2 calculated by the index calculation unit 51A2 and the blood mass index MA3 calculated by the index calculation unit 51A3. A method of calculating the resistance index is similar to that of the first embodiment. The processing unit 535 calculates the pulse pressure $\Delta P$ in accordance with the amplitude index calculated by the amplitude calculation unit 531 and the resistance index calculated by the resistance calculation unit 533 as in the first embodiment. In Modification Example 1, advantages similar to those of the first embodiment are obtained.

Modification Example 2

Figure 23:
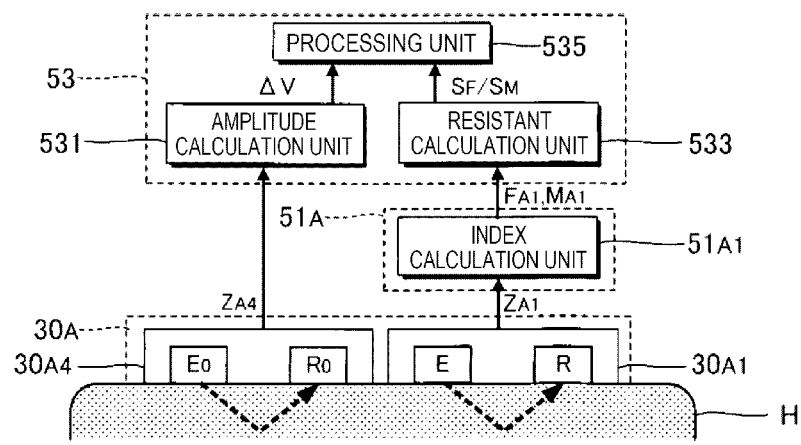
FIG. 23 is a diagram illustrating a configuration in which elements calculating a pulse pressure are focused on according to a modification example of the first embodiment.

FIG. 23 is a diagram illustrating a configuration in which elements calculating the pulse pressure $\Delta P$ are focused on according to a modification example (Modification Example 2) of the first embodiment. In the first embodiment, the ratio ($\Delta F/\Delta M$) correlating with the blood flow rate amplitude $\Delta V$ has been calculated as the amplitude index. In Modification Example 2, however, the blood flow rate amplitude $\Delta V$ is calculated as the amplitude index.

The detection unit 30A according to Modification Example 2 includes a detection device 30A4 in addition to the detection device 30A1 similar to that of the first embodiment. The detection device 30A1 according to Modification Example 2 has a configuration and a function similar to those of the first embodiment. The detection device 30A4 is an ultrasonic sensor module that generates the detection signal ZA4 in accordance with a state of the measurement region H. Specifically, the detection device 30A4 includes an emitting unit E0 and a receiving unit R0. The emitting unit E0 emits an ultrasonic wave to the measurement region H. On the other hand, the receiving unit R0 generates a detection signal ZA4 in accordance with a reception level of the ultrasonic wave emitted from the emitting unit E0 and passing through the inside of the measurement region H. For example, piezoelectric elements such as piezoelectric ceramics are used appropriately as the emitting unit E0 and the receiving unit R0.

The calculation unit 51A according to Modification Example 2 includes an index calculation unit 51A1 similar to that of the first embodiment. The index calculation unit 51A1 according to Modification Example 2 calculates the blood mass index MA1 and the blood flow index FA1 of the measurement region H from the detection signal ZA1 generated by the detection device 30A1 as in the first embodiment.

The pulse calculation unit 53 according to Modification Example 1 includes an amplitude calculation unit 531, a resistance calculation unit 533, and a processing unit 535 as in the first embodiment. The resistance calculation unit 533 according to Modification Example 2 calculates the resistance index (SF/SM) using the blood mass index MA1 and the blood flow index FA1 generated by the index calculation unit 51A1 as in the first embodiment.

The amplitude calculation unit 531 according to the first embodiment has calculated the amplitude index from the blood mass index MA1 and the blood flow index FA1 calculated by the index calculation unit 51A1. However, the amplitude calculation unit 531 according to Modification Example 2 directly calculates the amplitude index (the blood flow rate amplitude $\Delta V$) from the detection signal ZA4 generated by the detection device 30A4. The processing unit 535 calculates the pulse pressure $\Delta P$ in accordance with the amplitude index ($\Delta V$) calculated by the amplitude calculation unit 531 and the resistance index (SF/SM) calculated by the resistance calculation unit 533 as in the first embodiment.

In Modification Example 2, advantages similar to those of the first embodiment are obtained. In Modification Example 2, in particular, since the blood flow rate amplitude $\Delta V$ is calculated as the amplitude index, the pulse pressure $\Delta P$ can be calculated with higher precision than in the configuration in which the ratio ($\Delta F/\Delta M$) correlating with the blood flow rate amplitude $\Delta V$ is calculated as the amplitude index.

Modification Example 3

Figure 24:
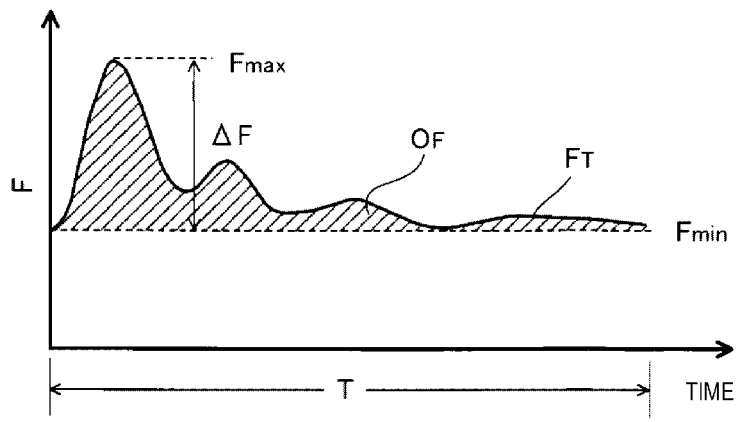
FIG. 24 is a graph illustrating a temporal change in a blood flow index.

FIG. 24 is a graph illustrating a temporal change FT in the blood flow index F. As exemplified in FIG. 24, an area OF of a region surrounded by a curve line indicating a temporal change FT in the blood flow index F and a straight line of a minimum value Fmin is equal to a product ($\Delta F \times SF$) of the amplitude $\Delta F$ and the blood flow integration value SF obtained by integrating the normalized blood flow indexes FN during the analysis period T. An area OM of a region surrounded by a curve line indicating the temporal change MT in the blood mass index M and a straight line of the minimum value Mmin is equal to a product ($\Delta M \times SM$) of the amplitude $\Delta M$ and the blood flow mass integration value SM obtained by integrating the normalized blood mass indexes MN during the analysis period T. Accordingly, Expression (13) below is derived from Expression (7) described above. As understood from Expression (13), the pulse pressure $\Delta P$ is expressed as a product the coefficient K and a ratio of the area OF and the area OM (specifically, a ratio of the area OF to the area OM). For the foregoing reason, the pulse pressure $\Delta P$ is calculated from the area OF and the area OM according to Modification Example 3.

$$\Delta P = K \times \frac{O_F}{O_M} \qquad (13)$$

Figure 25:
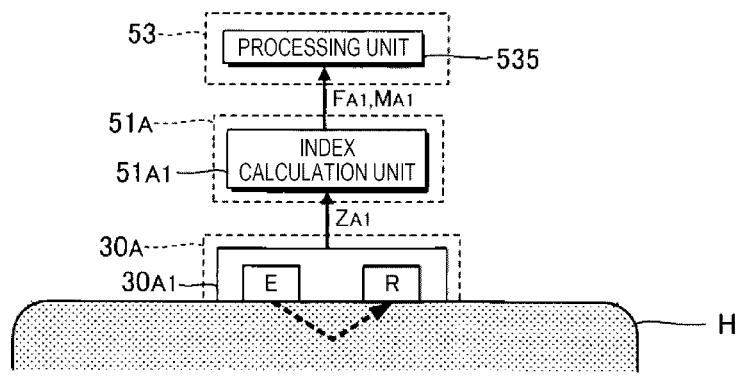
FIG. 25 is a diagram illustrating a configuration in which elements calculating a pulse pressure are focused on according to a modification example of the first embodiment.

FIG. 25 is a diagram illustrating a configuration in which elements calculating the pulse pressure ΔP are focused on according to a modification example (Modification Example 3) of the first embodiment. The configurations of the detection unit 30A and the calculation unit 51A in Modification Example 2 are the same as those of the first embodiment.

The pulse pressure calculation unit 53 according to Modification Example 3 has a configuration in which the amplitude calculation unit 531 and the resistance calculation unit 533 are deleted. The processing unit 535 according to Modification Example 3 calculates the pulse pressure ΔP from the blood mass index MA1 and the blood flow index FA1 calculated by the index calculation unit 51A1. The pulse pressure ΔP is calculated in accordance with the blood mass integration value SM obtained by integrating the blood mass indexes MA1 during the analysis period T and the blood flow integration value SF obtained by integrating the blood flow indexes FA1 during the analysis period T. In Modification Example 3, the processing unit 535 calculates the area OM as the blood mass integration value SM and calculates the area OF as the blood flow integration value SF. That is, in Modification Example 3, the process Sa13 of calculating the amplitude index in FIG. 17 and the process Sa14 of calculating the resistance index are omitted. Specifically, the processing unit 535 calculates the area OM and the area OF and calculates the pulse pressure ΔP by multiplying the ratio (OF/OM) of the area OF and the area OM by the coefficient K. The area OM is equivalent to the blood mass integration value SM obtained by integrating the blood mass indexes MA1 during the analysis period T and the area OF is equivalent to the blood flow integration value SF obtained by integrating the blood flow indexes FA1 during the analysis period T.

In Modification Example 3, the advantage that the pulse pressure ΔP is calculated and a cuff is unnecessary in principle is realized as in the first embodiment. Accordingly, it is possible to reduce a physical load of the subject and calculate the pulse pressure ΔP with high precision. In Modification Example 3, since it is unnecessary to calculate the amplitude ΔF and the amplitude ΔM and normalize the blood flow index FA1 and the blood mass index MA1, a processing load for calculating the pulse pressure ΔP is reduced.

Modification Example 4

FIG. 26 is a diagram illustrating a configuration in which elements calculating the pulse pressure ΔP are focused on according to a modification example (Modification Example 4) of the first embodiment. While the ratio of the blood flow integration value SF and the blood mass integration value SM is calculated as the resistance index in the first embodiment, the pulse wave velocity PWV is calculated as the resistance value in Modification Example 4.

The detection unit 30A according to Modification Example 4 includes a detection device 30A5 and a detection device 30A6 in addition to a detection device 30A1 similar to that of the first embodiment. The detection device 30A1 according to Modification Example 1 has a configuration and a function similar to those of the first embodiment and generates a detection signal ZA1 in accordance with a state of the measurement region H. The detection device 30A5 and the detection device 30A6 are, for example, optical sensor modules similar to that of the detection device 30A1. The detection device 30A5 generates a detection signal ZA5 in which a state of the measurement region H is reflected and the detection device 30A6 generates a detection signal ZA6 in which a state of the measurement region H is reflected.

The calculation unit 51A according to Modification Example 4 includes the index calculation unit 51A1 as in the first embodiment. The index calculation unit 51A1 according to Modification Example 4 calculates the blood mass index MA1 and the blood flow index FA1 of the measurement region H from the detection signal ZA1 generated by the detection device 30A1 as in the first embodiment.

The pulse pressure calculation unit 53 according to Modification Example 4 includes a PWV calculation unit 537 instead of the resistance calculation unit 533 of the first embodiment. The PWV calculation unit 537 calculates a pulse wave velocity PWV as a resistance index using the detection signal ZA5 generated by the detection device 30A5 and the detection signal ZA6 generated by the detection device 30A6. The pulse pressure calculation unit 53 calculates the pulse pressure ΔP in accordance with the amplitude index calculated by the amplitude calculation unit 531 and the resistance index calculated by the PWV calculation unit 537.

The elements (the detection unit 30B, the calculation unit 51B, and the average blood pressure calculation unit 55) calculating the average blood pressure pave are not limited to the configuration exemplified in FIG. 15.

Modification Example 5

Absorbance Abs of blood is changed in conjunction with pulsation of a blood vessel diameter. That is, the absorbance Abs correlates with a blood vessel diameter. Specifically, a relation between the absorbance Abs and the blood vessel diameter d is expressed in Expression (14) below. A sign C in Expression (14) is a molar absorbance coefficient and a sign c is red blood cell density. From the foregoing reason, according to Modification Example 5, an index related to the absorbance Abs of a biological body (hereinafter referred to as an "absorbance index") J is exemplified as a blood vessel diameter index calculated by the index calculation unit 51B1 in FIG. 15.

$$Abs = \varepsilon cd \tag{14}$$

The index calculation unit 51B1 according to Modification Example 5 calculates the absorbance index J and a blood flow index FB1 similar to that of the first embodiment from the detection signal ZB1 generated by the detection device 30B1. The absorbance Abs is expressed in Expression (15) below. A sign I in Expression (15) is an intensity of a signal component of the detection signal ZB1 and a sign I0 is an intensity of light incident on a measurement region (an intensity of light emitted from the light-emitting unit E). Expression (16) is derived from Expressions (14) and (15).

$$Abs = -\log(I/I_0) \tag{15}$$

$$d = \frac{-\log(I/I_0)}{\varepsilon c} \tag{16}$$

The molar absorbance coefficient c and the red blood cell density c can be set to predetermined values. That is, by calculating a common logarithm (log(I/I0)) of a ratio of the intensity I0 and the intensity I, it is possible to calculate the blood vessel diameter d. Accordingly, the index calculation unit 51B1 according to Modification Example 5 calculates the common logarithm (log(I/I0)) of the ratio of the intensity I0 and the intensity I as the absorbance index J. The intensity I0 is set to a predetermined value and the intensity I is calculated from a photoelectric volume pulse wave indicating a light reception level of light received from a biological body (the measurement region H). That is, the absorbance index J is calculated from the photoelectric volume pulse wave. The photoelectric volume pulse wave is generated from the detection signal ZB1 generated by the detection device 30B1. For example, the photoelectric volume pulse wave is generated through a filtering process of suppressing a high-frequency component of the detection signal ZB1 output by the detection device 30B1 and an amplification process of amplifying a signal subjected to the filtering process. The blood flow index FB1 is calculated in accordance with a method similar to that of the first embodiment.

The average blood pressure calculation unit 55 according to Modification Example 5 calculates the average blood pressure Pave from the absorbance index J and the blood flow index FB1 calculated by the index calculation unit 51B1. Specifically, the average blood pressure calculation unit 55 calculates the average blood pressure Pave in accordance with the average value Jave obtained by averaging the absorbance indexes J during the analysis period T and the average value Fave obtained by averaging the blood flow indexes F during the analysis period T. As described above, the absorbance index J correlates with the blood vessel diameter d2 and the blood flow index F is equivalent to the blood flow Q2. In consideration of the foregoing relation, Expression (17) is derived from Expressions (11) and (16) described above. The average blood pressure calculation unit 55 calculates the average blood pressure Pave by calculating Expression (17). A sign K is a coefficient determined in advance in accordance with the blood density ρ, the length L2 of an arteriole, and the like. The coefficient K is a coefficient determined in advance in accordance with the molar absorption coefficient c, the red blood cell c, the blood density ρ, the length L2 of an arteriole, and the like. As understood from Expression (17), the average blood pressure Pave according to Modification Example 5 in accordance with Fave/Jave$^4$. The coefficient K is set from, for example, a value actually measured using a cuff or the like and the calculation of Fave/Jave$^4$ in Expression (17) (for example, K=actually measured value/calculated value).

$$P_{ave} = K \times \frac{F_{ave}}{J_{ave}^4} \quad (17)$$

Content of the process Sa2 of calculating the average blood pressure Pave according to Modification Example 5 is similar to that of the first embodiment exemplified in FIG. 19. However, in step Sa21 of FIG. 19, the index calculation unit 51B1 calculates the absorbance index J instead of the blood mass index MB1. In step Sa231 of FIG. 20, the average blood pressure calculation unit 55 calculates the average value Jave of the absorbance indexes J instead of the average value Mave of the blood mass indexes MB1.

In Modification Example 5, advantages similar to those of the first embodiment are obtained. In Modification Example 5, in particular, since the absorbance index J calculated from the photoelectric volume pulse wave indicating a light reception level of light received from a biological body is used as the blood vessel diameter index, a processing load for calculating the blood vessel diameter index is reduced further than in the configuration of the first embodiment in which the blood mass index M calculated from the intensity spectrum is used as the blood vessel diameter index.

Modification Example 6

According to Modification Example 6, the average blood pressure Pave is calculated in accordance with the absorbance index J and the blood flow index FB1, as in Modification Example 5. However, while the detection signal ZB1 generated by the common light-receiving unit R is used in the calculation of the absorbance index J and the calculation of the blood flow index FB1 in Modification Example 5, a detection signal Z generated by a separate light-receiving unit R is used in calculation of the absorbance index J and the calculation of the blood flow index FB1 in Modification Example 6.

FIG. 27 is a diagram illustrating a configuration in which elements calculating the average blood pressure Pave are focused on according to Modification Example 6. The detection device 30B1 according to Modification Example 6 includes a light-emitting unit E and two light-receiving units R (R1 and R2). As in the first embodiment, the light-emitting unit E radiates a coherent laser light to the measurement region H (biological body) with a narrowband. Each light-receiving unit R receives the laser beam reflected inside the measurement region H as in Modification Example 5. The light-receiving units R are each installed at positions located at different distances from the light-emitting unit E. The positions at which the light-receiving units R are installed in the detection device 30B1 will be described in detail below. Specifically, the light-receiving unit R1 generates a detection signal ZB11 in accordance with a light reception level of the light passing through the inside of the measurement region H and the light-receiving unit R2 generates a detection signal ZB12 in accordance with a light reception level of the light passing through the inside of the measurement region H. The detection signal ZB11 is used in the calculation of the blood flow index FB1. On the other hand, the detection signal ZB12 is used in the calculation of the absorbance index J.

The index calculation unit 51B1 of the calculation unit 51B according to Modification Example 6 calculates the blood flow index FB1 from the detection signal ZB11 generated by the light-receiving unit R1 and calculates the absorbance index J from the detection signal ZB12 generated by the light-receiving unit R2. The blood flow index FB1 and the absorbance index J is calculated in accordance with a method similar to that of Modification Example 5. The average blood pressure calculation unit 55 according to Modification Example 6 calculates the average blood pressure Pave from the absorbance index J and the blood flow index FB1 calculated by the index calculation unit 51B1 as in Modification Example 5.

Hereinafter, the positions at which the light-receiving units R are installed in the detection device 30B1 will be described. Here, a frequency bandwidth (a frequency fL to fH in Expression (6b)) used in the calculation of the blood flow index FB1 in the detection signal ZB1 is different from a frequency bandwidth used in the calculation of the absorbance index J. A distance between the light-emitting unit E to the light-receiving unit R1 (for example, a distance between the centers of the light-emitting unit E and the light-receiving unit R1) in which the detection signal ZB11 with a high SN ratio can be obtained at a frequency bandwidth preferred in the calculation of the blood flow index FB1 is different from a distance between the light-emitting unit E to the light-receiving unit R2 (for example, a distance between the centers of the light-emitting unit E and the light-receiving unit R2) in which the detection signal ZB12 with a high SN ratio can be obtained at a frequency bandwidth preferred in the calculation of the absorbance index J.

FIG. 28 is a table illustrating quality of an SN ratio in a frequency bandwidth used in calculation of the blood flow index FB1 in the detection signal ZB11 and quality of an SN ratio in a frequency bandwidth used in calculation of the absorbance index J in the detection signal ZB12 in a plurality of cases in which a distance between the light-emitting unit E and the light-receiving unit R is changed. As ascertained from FIG. 28, the SN ratio of the frequency bandwidth used in the calculation of the blood flow index FB1 in the detection signal ZB11 indicates a highest value when the distance between the light-emitting unit E and the light-receiving unit R1 is equal to or greater than 0.5 mm and equal to or less than 2 mm. On the other hand, it was possible to obtain the knowledge that the SN ratio of the frequency bandwidth used in the calculation of the absorbance index J in the detection signal ZB12 is a highest value when the distance between the light-emitting unit E and the light-receiving unit R2 is equal to or greater than 3 mm and equal to or less than 5 mm.

On the basis of the foregoing knowledge, according to Modification Example 6, distances between the light-emitting unit E and the light reception units R1 and R2 are set separately. For example, the distance between the light-receiving unit R1 and the light-emitting unit E is set as a distance in which the detection signal ZB11 with a high SN ratio can be obtained at a frequency bandwidth preferred in the calculation of the blood flow index FB1, and the distance between the light-receiving unit R2 and the light-emitting unit E is set as a distance in which the detection signal ZB12 with a high SN ratio can be obtained at a frequency band preferred in the calculation of the absorbance index J. Specifically, on the basis of the result illustrated in FIG. 28, the distance between the light-emitting unit E and the light-receiving unit R1 is set to be equal to or greater than 0.5 mm and equal to or less than 2 mm, and the distance between the light-emitting unit E and the light-receiving unit R2 is set to be equal to or greater than 3 mm and equal to or less than 5 mm (preferably, 4 mm).

In Modification Example 6, advantages similar to those of Modification Example 5 are obtained. In Modification Example 6, in particular, since the light-receiving unit R1 calculating the blood flow index FB1 is separate from the light-receiving unit R2 calculating the absorbance index J, it is possible to generate the detection signal ZB11 with the high SN ratio at the frequency band preferred in the calculation of the blood flow index FB1 and the detection signal ZB12 with a high SN ratio at the frequency band preferred in the calculation the absorbance index J. Accordingly, the average blood pressure Pave can be calculated with higher precision than in the configuration in which the light-receiving unit R common to the calculation of the absorbance index J and the calculation of the blood flow index FB1 is used.

Modification Example 7

In the first embodiment, in the detection device 30A1 and the detection device 30B1, the detection signal Z generated by the common light-receiving unit R has been used in the calculation of the blood mass index M and the calculation of the blood flow index F, but the detection signals Z generated by separate light-receiving units can also be used in calculation of the blood vessel diameter index and calculation of the blood flow index F. Specifically, each detection device (30A1 and 30B1) includes a light-emitting unit E and two light-receiving units R (R1 and R2). An intensity spectrum of the detection signal Z generated by the light-receiving unit R1 is used in the calculation of the blood mass index M and an intensity spectrum of the detection signal Z generated by the light-receiving unit R2 is used in the calculation of the blood flow index F. Here, in the configuration of the first embodiment in which the detection signal Z generated by the common light-receiving unit R is used in the calculation of the blood mass index M and the calculation of the blood flow index F, an intensity spectrum common to the calculation of the blood mass index M and the calculation of the blood flow index F can be used.

Any combination of Modification Examples 1 to 4 related to the calculation of the pulse pressure ΔP and Modification Example 5 or 6 related to the calculation of the average blood pressure Pave is possible.

Second Embodiment

A second embodiment of the invention will be described. Elements similar to those of the first embodiment in operations or functions in each embodiment to be exemplified below, the reference numerals used in the description of the first embodiment are applied, and a detailed description of each element will be appropriately omitted.

Figure 29:
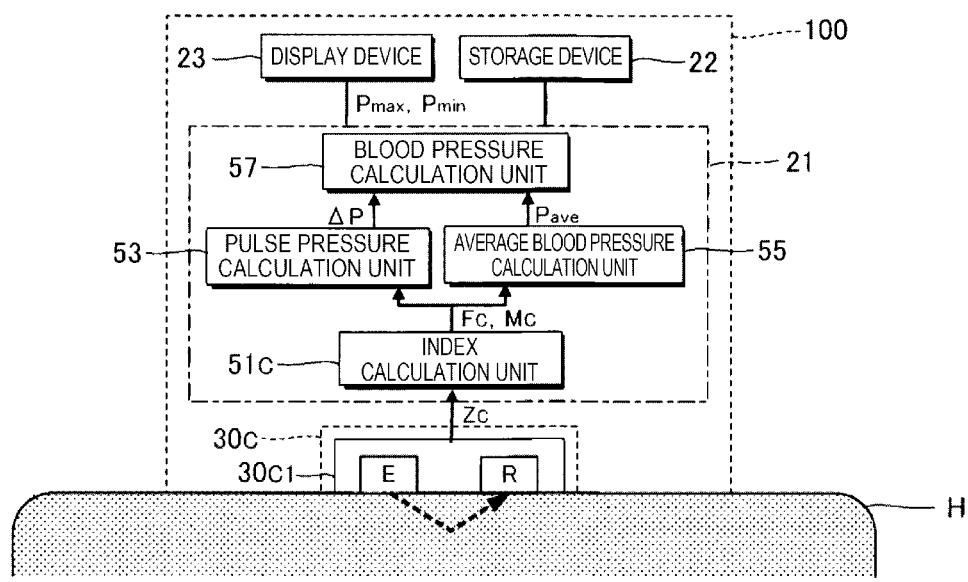
FIG. 29 is a diagram illustrating a configuration in which a function of biological analysis device is focused on according to a second embodiment.

FIG. 29 is a diagram illustrating a configuration in which a biological analysis device 100 is focused on according to the second embodiment. In the first embodiment, the detection signals Z (ZA1 and ZB1) generated by the separate detection devices (30A1 and 30B1) have been used in the calculation of the pulse pressure ΔP and the calculation of the average blood pressure Pave. In the second embodiment, however, a detection signal ZC generated by a single detection device 30C1 is used commonly in the calculation of the pulse pressure ΔP and the calculation of the average blood pressure Pave.

A biological analysis device 100 according to the second embodiment includes a detection unit 30C, a control device 21, a storage device 22, and a display device 23. The detection unit 30C includes the detection device 30C1. The detection device 30C1 has a configuration similar to the detection device 30A1 of the detection unit 30A in the first embodiment and generates a detection signal ZC indicating a light reception level of light passing through the inside of a measurement region H. The detection device 30C1 is appropriately installed at a position (for example, the back of a wrist) facing an arteriole inside the measurement region H. That is, the detection signal ZC in which a state of the arteriole is reflected is generated.

The control device 21 according to the second embodiment includes the index calculation unit 51C, the pulse pressure calculation unit 53, the average blood pressure calculation unit 55, and the blood pressure calculation unit 57. The index calculation unit 51C calculates the blood mass index MC and the blood flow index FC from the detection signal ZC generated by the detection device 30C1. The blood mass index MC is calculated similarly to the blood mass index MA1 of the first embodiment and the blood flow index FC is calculated similarly to the blood flow index FA1 of the first embodiment. The pulse pressure calculation unit 53 according to the second embodiment calculates the pulse pressure ΔP from the blood mass index MC and the blood flow index FC in accordance with a method similar to that of the first embodiment. The average blood pressure calculation unit 55 according to the second embodiment calculates the average blood pressure Pave from the blood mass index MC and the blood flow index FC in accordance with a method similar to that of the first embodiment. The blood pressure calculation unit 57 according to the second embodiment calculates the systolic blood pressure Pmax and the diastolic blood pressure Pmin in accordance with the pulse pressure ΔP and the average blood pressure Pave as in the first embodiment.

In the second embodiment, advantages similar to those of the first embodiment are obtained. In the second embodiment, since the detection signal ZC generated by the detection device 30C1 common to the calculation of the pulse pressure ΔP and the calculation of the average blood pressure Pave is used, the biological analysis device 100 can be miniaturized further than in the configuration in which the detection signals Z generated by the separate detection devices are used in the calculation of the pulse pressure ΔP and the calculation of the average blood pressure Pave. However, according to the configuration of the first embodiment in which the detection signals Z (ZA1 and ZB1) generated by the separate detection devices (30A1 and 30B1) are used in the calculation of the pulse pressure ΔP and the calculation of the average blood pressure Pave, it is possible to generate the detection signals Z in which a state of a part appropriate for the calculation of the pulse pressure ΔP and the calculation of the average blood pressure Pave is reflected.

In the second embodiment, since the blood mass index MC and the blood flow index FC calculated by the index calculation unit 51C common to the calculation of the pulse pressure ΔP and the calculation of the average blood pressure Pave are used, a processing load for calculating the systolic blood pressure Pmax and the diastolic blood pressure Pmin is reduced further than in the configuration in which the blood mass index M and the blood flow index F calculated by the separate index calculation units 51A are used in the calculation of the pulse pressure ΔP and the calculation of the average blood pressure Pave.

In the biological analysis device 100 according to the second embodiment, the elements (the detection device 30A5, the detection device 30A6, and the PWV calculation unit 537) calculating the pulse wave velocity PWV exemplified in FIG. 26 may be replaced with the element (the resistance calculation unit 533) calculating the resistance index.

In the second embodiment in which the detection signal ZC generated by the detection device 30C1 is used commonly in the calculation of the pulse pressure ΔP and the calculation of the average blood pressure Pave, the detection signal ZC preferred for the calculation of the pulse pressure ΔP and the calculation of the average blood pressure Pave can be generated by installing the detection device 30C1 at a position close to an arteriole. When a wrist is the measurement region H, for example, the detection device 30C1 is installed on the surface of the back of the wrist. When an upper arm is the measurement region H, for example, the detection device 30C1 is installed on an opposite surface to a trunk in the upper arm.

Third Embodiment

Figure 30:
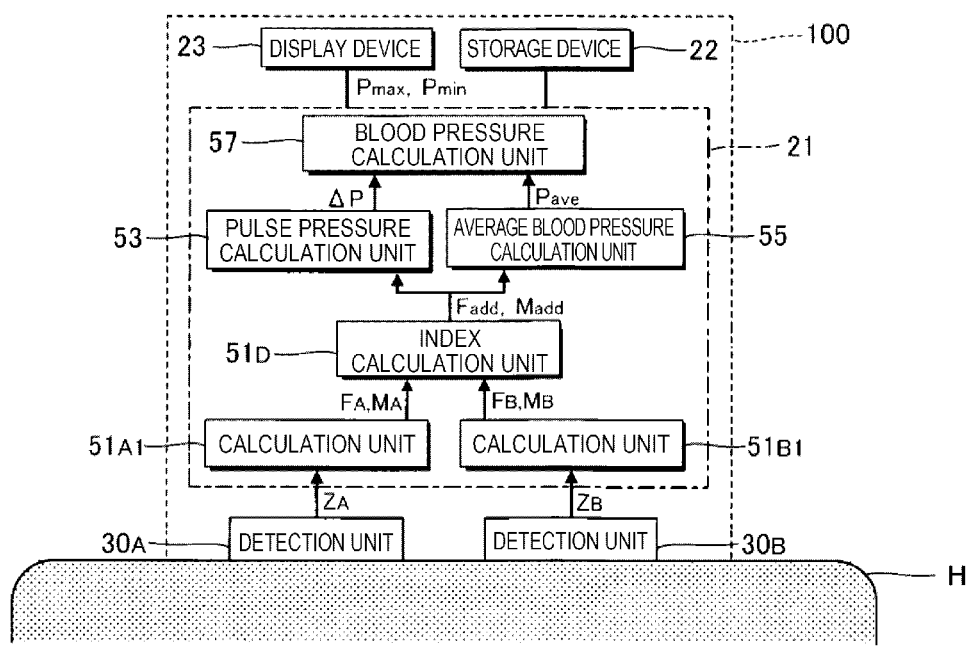
FIG. 30 is a diagram illustrating a configuration in which a function of a biological analysis device is focused on according to a third embodiment.

FIG. 30 is a diagram illustrating a configuration in which the biological analysis device 100 is focused on according to a third embodiment. In the biological analysis device 100 according to the third embodiment, the index calculation unit 51D is added to the biological analysis device 100 according to the first embodiment. The detection unit 30A (the detection device 30A1) and the calculation unit 51A (the index calculation unit 51A1), and the detection unit 30B (the detection device 30B1) and the calculation unit 51B (the index calculation unit 51B1) have configurations and functions similar to those of the first embodiment. For example, the detection unit 30A is installed on the palm of the wrist and the detection device 30B is installed on the back of the wrist.

The index calculation unit 51D adds or averages the indexes calculated by the calculation unit 51A and the indexes generated by the calculation unit 51B. Specifically, the index calculation unit 51D calculates an added value Madd obtained by adding the blood mass index MA calculated by the calculation unit 51A and the blood mass index MB calculated by the calculation unit 51B. The index calculation unit 51D calculates an added value Fadd obtained by adding the blood flow index FA calculated by the calculation unit 51A and the blood flow index FB calculated by the calculation unit 51B. The index calculation unit 51D may calculate an average value obtained by averaging the blood mass index MA and the blood mass index MB and an average value obtained by averaging the blood flow index FA and the blood flow index FB.

The pulse pressure calculation unit 53 according to the third embodiment calculates the pulse pressure ΔP using the added value Madd and the added value Fadd calculated by the index calculation unit 51D in accordance with a method similar to that of the first embodiment. Specifically, the pulse pressure calculation unit 53 calculates the amplitude index and the resistance index from a temporal change in the added value Madd and a temporal change in the added value Fadd and calculates the pulse pressure ΔP from the amplitude index and the resistance index. The average blood pressure calculation unit 55 according to the third embodiment calculates the average blood pressure Pave using the added value Madd and the added value Fadd calculated by the index calculation unit 51D in accordance with a method similar to the first embodiment. Specifically, the average blood pressure calculation unit 55 calculates the average blood pressure Pave in accordance with $Fadd/Madd^{4/3}$. The blood pressure calculation unit 57 calculates the systolic blood pressure Pmax and the diastolic blood pressure Pmin as in the first embodiment.

Figure 31:
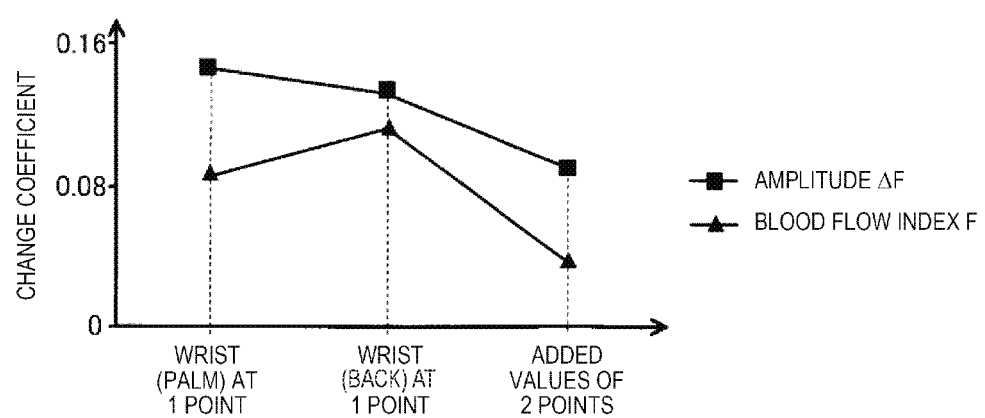
FIG. 31 is a graph illustrating a change coefficient of an average value of amplitudes of blood flow indexes over a plurality of analysis periods and a change coefficient of an average value of the blood flow indexes over the plurality of analysis periods.

FIG. 31 is a graph illustrating a change coefficient of an average value of the amplitudes ΔF over the plurality of analysis periods T and a change coefficient of an average value of the blood flow indexes F over the plurality of analysis periods T. FIG. 31 illustrates a case in which the blood flow index F is calculated from the detection signal Z generated by one detection device (a detection device installed on the palm of the wrist and a detection device installed on the back of the wrist) and a case in which the blood flow index F calculated from the detection signals generated by two detection devices. The change coefficient is an index indicating the degree of a variation between a plurality of numerical values and is specifically a ratio (σ/x) of a standard deviation σ calculated from measurement values in a plurality of times and an average value x obtained by averaging measured values a plurality of times. As the change coefficient is smaller, a variation between the blood flow index F and the amplitude ΔF is smaller. As ascertained from FIG. 31, the change coefficient in the added value Fadd of the blood flow index F calculated from two detection signals is less than the change coefficient of the blood flow index F calculated from a detection signal at one point in both the amplitude ΔF and the blood flow index F. Accordingly, according to the third embodiment in which the systolic blood pressure Pmax and the diastolic blood pressure Pmin are calculated from the added value obtained by adding the indexes calculated using the two detection devices 30A1 and 30B1, the systolic blood pressure Pmax and the diastolic blood pressure Pmin can be calculated with higher precision than in the configuration (for example, in the first embodiment) in which each index is calculated using the detection signal generated by one detection device.

Fourth Embodiment

Figure 32:
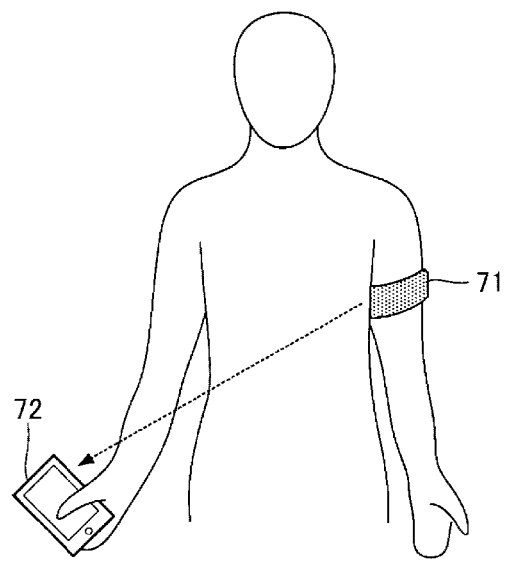
FIG. 32 is a schematic diagram illustrating a use example of a biological analysis device according to a fourth embodiment.
Figure 33:
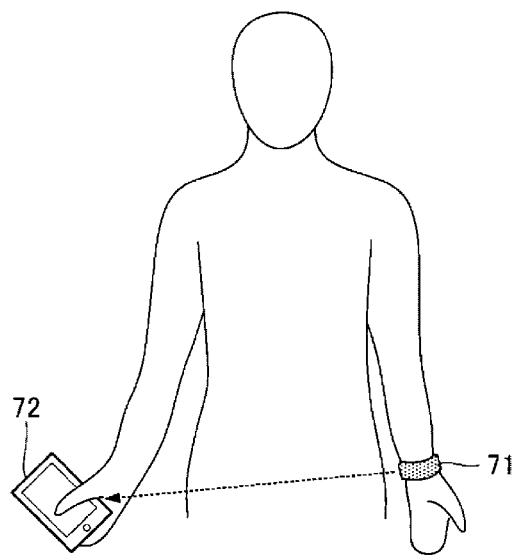
FIG. 33 is a schematic diagram illustrating another use example of the biological analysis device according to the fourth embodiment.

FIG. 32 is a schematic diagram illustrating a use example of a biological analysis device 100 according to a fourth embodiment. As exemplified in FIG. 32, the biological analysis device 100 includes a detection unit 71 and a display unit 72 configured to be separate from each other. The detection unit 71 includes detection units 30 (30A and 30B) exemplified in the first embodiment. FIG. 32 exemplifies the detection unit 71 worn on an upper arm of a subject. As exemplified in FIG. 33, the detection unit 71 worn on a wrist of the subject is also appropriate.

The display unit 72 includes the display device 23 exemplified in each of the above-described embodiments. For example, an information terminal such as a mobile phone or a smartphone is an appropriate example of the display unit 72. Here, any specific form of the display unit 72 is used. For example, a wrist watch type information terminal which can be carried by the subject or an information terminal dedicated for the biological analysis device 100 may be used as the display unit 72.

An element (hereinafter referred to as a "calculation processing unit") calculating the systolic blood pressure Pmax and the diastolic blood pressure Pmin from the detection signal Z is mounted on the display unit 72, for example. The calculation processing unit includes the elements exemplified in FIG. 3 (the calculation unit 51A, the calculation unit 51B, the pulse pressure calculation unit 53, the average blood pressure calculation unit 55, and the blood pressure calculation unit 57). The detection signals Z (ZA and ZB) generated by the detection unit 30 of the detection unit 71 are transmitted to the display unit 72 in a wired or wireless manner. The calculation processing unit of the display unit 72 calculates the systolic blood pressure Pmax and the diastolic blood pressure Pmin from the detection signal ZA and the detection signal ZB and displays the systolic blood pressure Pmax and the diastolic blood pressure Pmin on the display device 23.

The calculation processing unit may be mounted on the detection unit 71. The calculation processing unit calculates the systolic blood pressure Pmax and the diastolic blood pressure Pmin from the detection signal ZA and the detection signal ZB generated by the detection unit 30 and transmits data for displaying the systolic blood pressure Pmax and the diastolic blood pressure Pmin to the display unit 72 in a wired or wireless manner. The display device 23 of the display unit 72 displays the systolic blood pressure Pmax and the diastolic blood pressure Pmin indicated by the data received from the detection unit 71. The fourth embodiment can also be applied to the second embodiment and the third embodiment.

Fifth Embodiment

Figure 34:
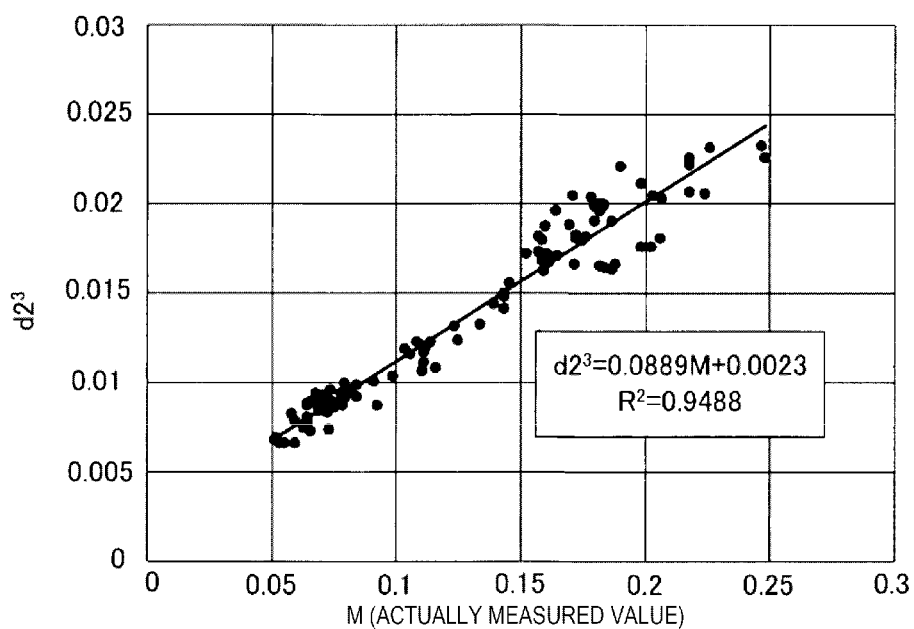
FIG. 34 is a graph illustrating a relation between actually measured values of a blood mass index and a third power of a blood vessel diameter according to a fifth embodiment.

FIG. 34 is a graph illustrating a relation between actually measured values of the blood mass index M and a third power ($d2^3$) of the blood vessel diameter d2 calculated from the actually measured values of the blood flow index F and the actually measured values of the average blood pressure Pave. The actually measured value of the blood mass index M and the actually measured value of the blood flow index F are measured using, for example, a laser Doppler blood flowmeter. The average blood pressure Pave is measured using a cuff or the like. FIG. 34 illustrates a result measured on a plurality of subjects. As described above, the blood vessel diameter d2 is equivalent to a cubic root ($M^{1/3}$) of the blood mass index M. Therefore, Expression (18) below is derived from Expression (12). $d2^3$ is calculated using Expression (18).

$$d2^3 = K\left(\frac{F_{ave}}{P_{ave}}\right)^{\frac{3}{4}} \quad (18)$$

As ascertained from FIG. 34, it is possible to obtain the knowledge that a regression line indicating a relation between $d2^3$ and the actually measured value of the blood mass index M is expressed by a linear function that has a slope and an intercept. When a is a coefficient indicating the slope and b is a coefficient indicating the intercept, $d2^3$ is expressed in Expression (19) below. FIG. 34 exemplifies a case in which the coefficient a is 0.0889 and the coefficient b is 0.0023. The actually measured value of blood mass index M and $d2^3$ have high correlation, it can be understood that the correlation is appropriately approximate by Expression (19). A correlation coefficient $R^2$ in FIG. 34 is 0.9488.

$$d2^3 = a \times M + b \quad (19)$$

On the premise that the third power of the blood vessel diameter d2 is equivalent to the blood mass index M and the blood flow index F is equivalent to the blood flow Q2, Expression (11) described above is modified to Expression (20) below. A sign K' in Expression (20) is a coefficient determined in advance in accordance with the blood density ρ, a length L2 of an arteriole, and the like as in the coefficient K in Expression (12).

$$P_{ave} = K' \times \frac{F}{(\alpha \times M + b)^{\frac{4}{3}}} \quad (20)$$

Figure 35:
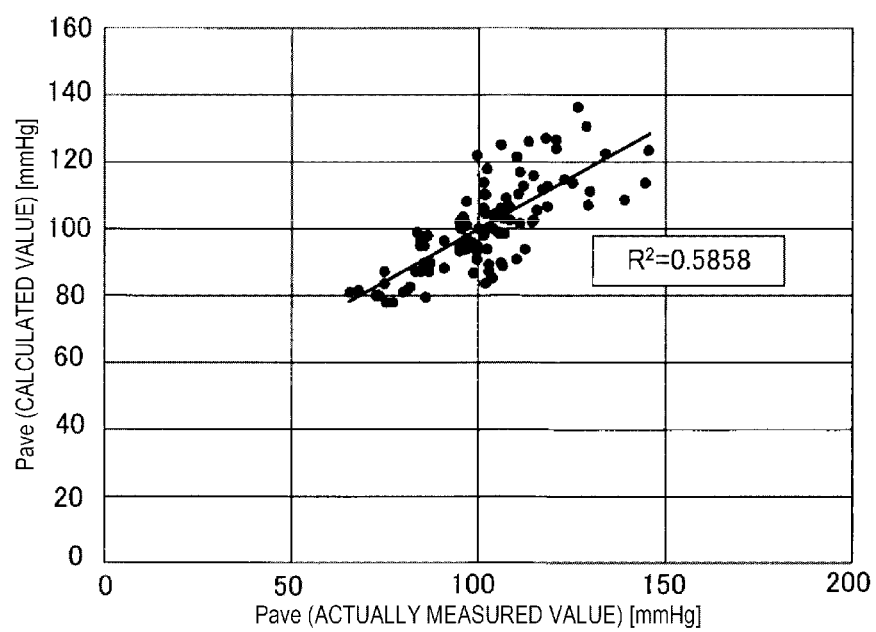
FIG. 35 is a graph illustrating a relation between average blood pressures and average blood pressures (calculated values) according to the fifth embodiment.

FIG. 35 is a graph illustrating a relation between actually measured values of the average blood pressure Pave measured by a cuff or the like and the calculated values of the average blood pressure Pave calculated from Expression (20). Negative correlation is observed between the actually measured value of the average blood pressure Pave and a calculated value of the average blood pressure Pave observed on the assumption that $d2^3$ has no intercept in some cases. In contrast, as ascertained in FIG. 35, positive correlation was observed between the actually measured value of the average blood pressure Pave and the calculated value of the average blood pressure Pave calculated by Expression (20). The correlation coefficient $R^2$ in FIG. 34 is 0.5858. On the basis of the foregoing knowledge, the average blood pressure Pave is calculated using Expression (20) in the fifth embodiment. That is, the average blood pressure Pave is calculated by $F_{ave}/(a \times M_{ave}+b)^{4/3}$.

The coefficients a and b in Expression (20) are statistically set, for example, using the actually measured values (the average blood pressure Pave, the blood mass index M, and the blood flow index F) calculated from a plurality of subjects. The coefficients a and b may be set for each user of the biological analysis device 100 or the coefficients a and b common to users may be set. When the coefficients a and b are set for each user, it is necessary to correct the coefficients a and b using actually measured values measured for each user. On the other hand, when the coefficients a and b common to users are set, there is the advantage that correction is not necessary for each user. One of the coefficients a and b may be set to be common to the users and the other may be set for each user.

As understood from the foregoing description, according to the fifth embodiment, the average blood pressure Pave is calculated in accordance with $Fave/(a \times Mave+b)^{4/3}$ which is observed to have positive correlation with the actually measured value of the average blood pressure Pave. Therefore, it is possible to calculate the average blood pressure Pave with high precision. When the coefficients a and b are set to be common to the users, there is the advantage that the correction is not necessary at the time of using the biological analysis device 100. The configuration of the fifth embodiment can be applied to any of the first to fourth embodiments.

Sixth Embodiment

Noise distributed with a substantially equal intensity in a whole region on the frequency axis (hereinafter referred to as "background noise") can be contained in the intensity spectrum related to a frequency of the detection signal ZB1 according to the first embodiment. The background noise is shot noise unique to an electric circuit included in the biological analysis device 100 or noise caused due to an electromagnetic wave in an installation environment of the biological analysis device 100. In a sixth embodiment, the background noise is reduced from an intensity spectrum specified from the detection signal ZB1, and the blood mass index M and the blood flow index F are calculated.

The detection device 30B1 according to the sixth embodiment generates a signal indicating the background noise (hereinafter referred to as an "observation signal") in addition to the detection signal ZB1 exemplified in each of the above-described embodiments. The observation signal is generated in a state in which a blood flow is not observed. For example, a signal output by the light-receiving unit R is generated as an observation signal in a state in which the light-emitting unit E radiates light to a stationary object with low reflectance without including a moving object. A signal output by the light-receiving unit R may be used as an observation signal in a state in which light is not radiated to a stationary object. A signal output by the light-receiving unit R may be used as an observation signal in a state in which the measurement region H or a position upstream from the measurement region H is stopped from bleeding by a cuff or the like. As understood from the foregoing description, an observation signal containing no component originating from a blood flow of the measurement region H is generated. That is, an observation signal indicating the background noise in a case in which the blood mass index M and the blood flow index F of the measurement region H are calculated is generated.

The index calculation unit 51B1 according to the sixth embodiment subtracts an intensity G(f)bg of the background noise from an intensity G(f) at each frequency f in an intensity spectrum related to the frequency of the detection signal ZB1 and calculates the blood mass index M and the blood flow index F. The intensity G(f)bg of the background noise is an intensity at each frequency f in the intensity spectrum calculated from the observation signal. A value obtained by smoothing the intensity G(f)bg of the background noise (for example, moving average) may be subtracted from the intensity G(f). The intensity G(f)bg may be smoothed on either the time axis or the frequency axis.

Specifically, the index calculation unit 51B1 specifies a correction intensity G(f)c by subtracting the intensity G(f)bg from the intensity G(f) at each frequency f. The correction intensity G(f)c is expressed in Expression (21) below.

$$G(f)c = G(f) - G(f)bg \quad (21)$$

The blood mass index M and the blood flow index F are calculated using the correction intensity G(f)c calculated from Expression (21). That is, the blood mass index M and the blood flow index F from which an influence of the background noise is reduced are calculated. As in each of the above-described embodiments, Expression (5a) or (5b) is used in the calculation of the blood mass index M, and Expression (6a) or (6b) is used in the calculation of the blood flow index F.

As understood from the foregoing description, according to the sixth embodiment, the intensity G(f)bg of the background noise is subtracted from the intensity G(f) at each frequency f in the intensity spectrum of the detection signal ZB1 to calculate the blood mass index M and the blood flow index F. Accordingly, the blood mass index M and the blood flow index F from which an influence of the background noise is reduced are calculated. That is, it is possible to calculate the average blood pressure Pave with high precision. In the foregoing description, the average blood pressure Pave has been focused on, but Expression (21) is used similarly for the blood mass index M and the blood flow index F used in the calculation of the pulse pressure ΔP. That is, it is possible to calculate the pulse pressure ΔP with high precision from the blood mass index M and the blood flow index F from which an influence of the background noise is reduced.

As ascertained from Expression (6a) or (6b), the blood flow index F is calculated by multiplying the intensity G(f) by the frequency f (that is, using a frequency weighted intensity spectrum (f×G(f))). Accordingly, there is a tendency that the influence of the background noise increases with respect to the blood flow index F as the frequency f increases. The configuration in which the background noise is reduced from the intensity spectrum according to the sixth embodiment is particularly effective when the blood flow index F is calculated. The configuration of the sixth embodiment can be used to reduce the background noise from the intensity spectrum of the optically detected detection signal in the first to fifth embodiments.

Seventh Embodiment

When the background noise is removed at a frequency bandwidth (hereinafter referred to as a "designation bandwidth") in which the intensity G(f) is not changed in accordance with pulsation of the measurement region H in the intensity spectrum of the detection signal ZB1 in the sixth embodiment, the intensity G(f) becomes closes to 0. As the intensity G(f) in the designation bandwidth is closer to 0, the background noise is paraphrased as being removed with high precision. Accordingly, in a seventh embodiment, the intensity G(f)bg is subtracted from the intensity G(f) so that a result obtained by subtracting the intensity G(f)bg from the intensity G(f) is closer to 0 in the designation bandwidth. The designation bandwidth is, for example, a bandwidth equal to or greater than 25 kHz or equal to or less than 30 kHz. The designation bandwidth is not limited to the foregoing example. For example, the designation bandwidth is changed appropriately in accordance with the kind of measurement region H.

The index calculation unit 51B1 according to the seventh embodiment calculates the blood mass index M and the blood flow index F by subtracting the intensity G(f)bg of the background noise from the intensity G(f) at each frequency f in the intensity spectrum related to the frequency of the detection signal ZB1 as in the sixth embodiment. Specifically, the index calculation unit 51B1 calculates the correction intensity G(f)c by subtracting the intensity G(f)bg from the intensity G(f) so that the result obtained by subtracting the intensity G(f)bg from the intensity G(f) is close to 0 in the designation bandwidth. The correction intensity G(f)c according to the seventh embodiment is expressed in Expression (22) below.

$$G(f)c = G(f) - C \times G(f)bg \quad (22)$$

A sign C in Expression (22) is a coefficient set so that the correction intensity G(f)c in the designation bandwidth is closer to 0. Specifically, the coefficient C is set so that a value calculated from Expression (23) below is minimum (ideally, 0). A sign fmax of Expression (22) is an upper limit of the frequency of the designation bandwidth and fmin is a lower limit of the frequency of the designation bandwidth. The coefficient C may be set in accordance with the frequency f. For example, the coefficient C different for each bandwidth segmented into a plurality of pieces on the frequency axis may be set.

$$\sum_{f_{min}}^{f_{max}} (G(f) - C \times G(f)bg)^2 \quad (23)$$

As ascertained from Expression (22), the correction intensity G(f)c is calculated by subtracting the intensity G(f)bg multiplied by the coefficient C from the intensity G(f). The index calculation unit 51B1 calculates the blood mass index M and the blood flow index F using the correction intensity G(f)c calculated by Expression (22) at each frequency f. As in each of the above-described embodiments, Expression (5a) or (5b) is used in the calculation of the blood mass index M, and Expression (6a) or (6b) is used in the calculation of the blood flow index F.

Figure 36:
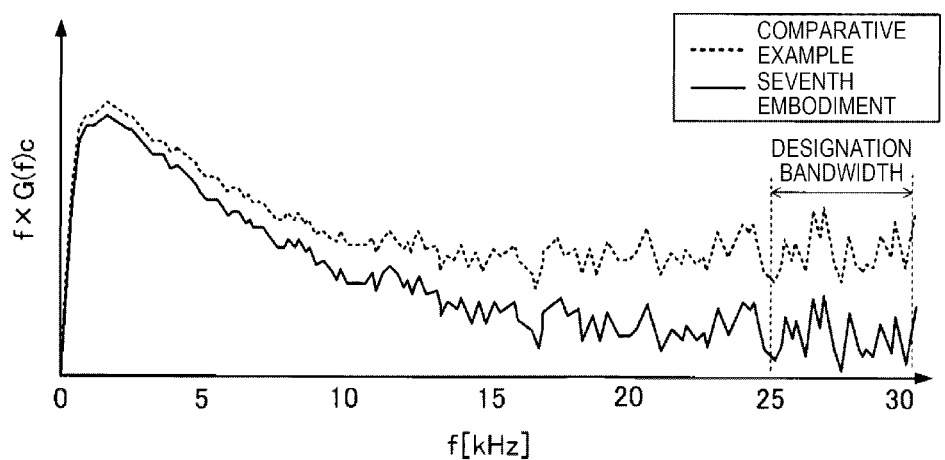
FIG. 36 is a graph illustrating a frequency weighted intensity spectrum according to a seventh embodiment and a comparative example.

FIG. 36 is graph illustrating the frequency weighted intensity spectrum (f×G(f)c) calculated in a configuration in which the correction intensity G(f)c is calculated without multiplying the intensity G(f)b by the coefficient C (hereinafter referred to as a "comparative example") and the frequency weighted intensity spectrum (f×G(f)c) calculated from the correction intensity G(f)c by calculating Expression (22). As ascertained from FIG. 36, in the configuration of the seventh embodiment, the frequency weighted intensity spectrum (f×G(f)c) in which the background noise is reduced with higher precision is calculated than in the comparative example. In particular, the background noise is effectively reduced on a high bandwidth in which an influence of the background noise increases and the frequency weighted intensity spectrum (f×G(f)c) is calculated. That is, it is possible to calculate the blood flow index F from which the background noise is effectively reduced over the whole frequency axis.

Figure 37:
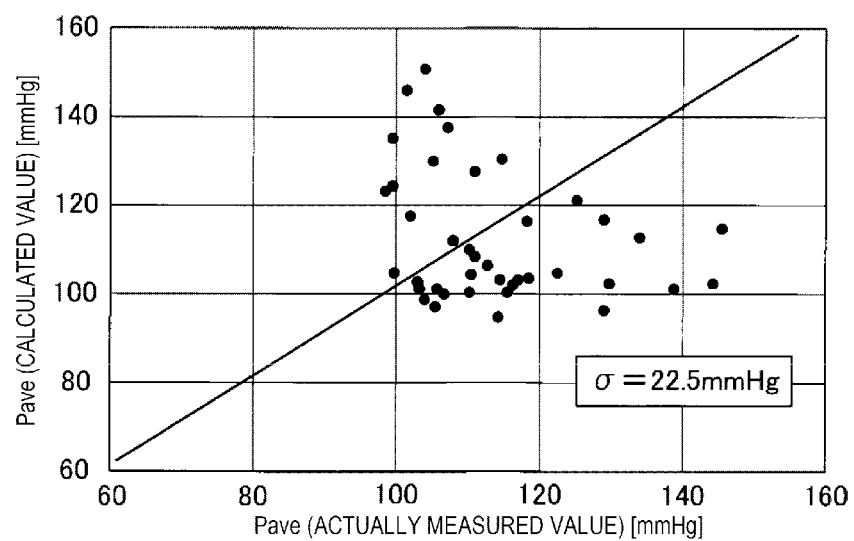
FIG. 37 is a graph illustrating a relation between an average blood pressure (calculated value) in the comparative example and an average blood pressure (actually measured value).
Figure 38:
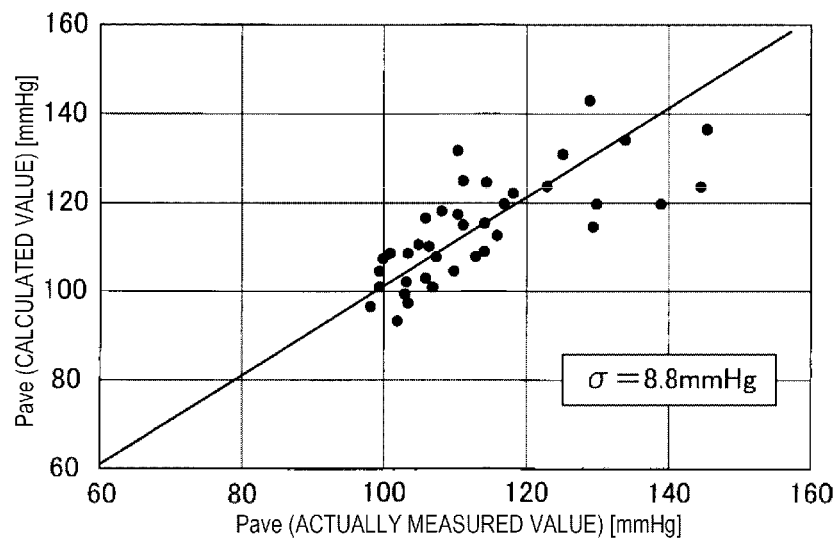
FIG. 38 is a graph illustrating a relation between an average blood pressure (calculated value) and an average blood pressure (actually measured value) according to the seventh embodiment.

FIG. 37 is a graph illustrating a relation between a calculated value of the average blood pressure Pave calculated in the comparative example and actually measured value of the average blood pressure Pave measured by a cuff or the like. FIG. 38 is a graph illustrating a relation between a calculated value of the average blood pressure Pave calculated in the configuration of the seventh embodiment and an actually measured value of the average blood pressure Pave measured by a cuff or the like. As ascertained from FIGS. 37 and 38, according to the seventh embodiment, higher correlation (positive correlation) is observed between the calculated value of the average blood pressure Pave and the actually measured value of the average blood pressure Pave than in the comparative example. While a standard deviation σ of the calculated values of the average blood pressure Pave in FIG. 37 is 22.5 mmHg, the standard deviation σ of the calculated values of the average blood pressure Pave in FIG. 38 is 8.8 mmHg. As described above, according to the seventh embodiment, it can be understood that the average blood pressure Pave can be calculated with higher precision than in the comparative example. In the foregoing description, the average blood pressure Pave has been focused on, but Expression (22) is used similarly in the blood mass index M and the blood flow index F used in the calculation of the pulse pressure ΔP.

In the seventh embodiment, advantages similar to those of the first embodiment are obtained. In the seventh embodiment, the blood mass index M and the blood flow index F in which the influence of the background noise is reduced are calculated as in the sixth embodiment. According to the seventh embodiment, in particular, the blood mass index M and the blood flow index F are calculated by subtracting the intensity G(f)bg from the intensity G(f) so that the result obtained by subtracting the intensity G(f)bg from the intensity G(f) is closer to 0 in the designation bandwidth. Accordingly, it is possible to reduce the influence of the background noise with higher precision and calculate the blood mass index M and the blood flow index F than in the comparative example.

Modification Examples

Each of the embodiments exemplified above can be modified in various forms. Specific modification aspects will be exemplified below. Two or more selected arbitrarily from the following examples can also be merged appropriately.

(1) In each of the above-described embodiments, the systolic blood pressure Pmax and the diastolic blood pressure Pmin have been displayed on the display device 23, but the pulse pressure ΔP and the average blood pressure Pave used in the calculation of the systolic blood pressure Pmax and the diastolic blood pressure Pmin may be displayed on the display device 23. That is, the pulse pressure ΔP and the average blood pressure Pave are used as biological information separate from the systolic blood pressure Pmax and the diastolic blood pressure Pmin.

(2) Any kind of detection device generating the detection signal Z used in the calculation of the blood mass index M and the absorbance index J used in the calculation of the pulse pressure ΔP and the average blood pressure Pave can be used. For example, an optical sensor module that emits coherent light or incoherent light and generates the detection signal Z in accordance with a state of the measurement region H, a pressure sensor that generates the detection signal Z indicating displacement of a surface of the measurement region H, or an ultrasonic sensor module that generates the detection signal Z in accordance with a state of the measurement region H can be appropriately adopted. A configuration is preferable in which at least one of the pulse pressure index and the average blood pressure index is calculated in accordance with the blood flow index F calculated from an intensity spectrum related to the frequency of the light reflected and received inside a biological body through radiation of a laser beam.

(3) In each of the above-described embodiments, the blood pressure calculation unit 57 has calculated the systolic blood pressure Pmax and the diastolic blood pressure Pmin, but indexes calculated by the blood pressure calculation unit 57 are not limited to the systolic blood pressure Pmax and the diastolic blood pressure Pmin. For example, the blood pressure calculation unit 57 may specify indexes (for example, abnormality/high side/normality or the like) indicating states of the systolic blood pressure Pmax and the diastolic blood pressure Pmin of a subject using the calculated systolic blood pressure Pmax and diastolic blood pressure Pmin.

(4) In each of the above-described embodiments, as ascertained from Expression (1), the systolic blood pressure Pmax has been calculated adding the value obtained by multiplying the pulse pressure ΔP by ⅔ to the average blood pressure Pave, but the coefficient by which the pulse pressure ΔP in Expression (1) is multiplied is not limited to ⅔. For the diastolic blood pressure Pmin, a coefficient other than ⅓ may be similarly multiplied to the pulse pressure ΔP in Expression (2). When a coefficient to be multiplied to the pulse pressure ΔP in Expression (1) is set as a first coefficient, the systolic blood pressure Pmax is calculated by adding a value obtained by multiplying the pulse pressure ΔP by the first coefficient to the average blood pressure Pave. On the other hand, when a coefficient to be multiplied by the pulse pressure ΔP in Expression (2) is set as a second coefficient, the diastolic blood pressure Pmin is calculated by subtracting a value obtained by multiplying the pulse pressure ΔP by the second coefficient to the average blood pressure Pave. Any value can be set to the first and second coefficients.

The methods of calculating the systolic blood pressure Pmax and the diastolic blood pressure Pmin are not limited to the calculation of Expressions (1) and (2) described above. When the systolic blood pressure Pmax and the diastolic blood pressure Pmin are calculated in accordance with the pulse pressure ΔP and the average blood pressure Pave, any specific calculation method can be used. In each of the above-described embodiments in which the systolic blood pressure Pmax is calculated by adding the value obtained by multiplying the pulse pressure ΔP by the first coefficient to the average blood pressure Pave and the diastolic blood pressure Pmin is calculated by subtracting the value obtained by multiplying the pulse pressure ΔP by the second coefficient from the average blood pressure Pave, it is possible to calculate the systolic blood pressure Pmax and the diastolic blood pressure Pmin with high precision using the tendency that the value obtained by adding the value obtained by multiplying the pulse pressure ΔP by the first coefficient to the average blood pressure Pave is approximate to the systolic blood pressure Pmax and the value obtained by subtracting the value obtained by multiplying the pulse pressure ΔP by the second coefficient from the average blood pressure Pave is approximate to the diastolic blood pressure Pmin.

(5) In each of the above-described embodiments, the pulse pressure calculation unit 53 has calculated the pulse pressure ΔP, but the index calculated by the pulse pressure calculation unit 53 is not limited to the pulse pressure ΔP. For example, the pulse pressure calculation unit 53 can also calculate a value calculated by substituting the pulse pressure ΔP to a predetermined function or a value obtained by multiplying the pulse pressure ΔP by a coefficient. As understood from the above description, the index calculated by the pulse pressure calculation unit 53 is expressed comprehensively as an index related to the pulse pressure ΔP (hereinafter referred to as a "pulse pressure index") and the pulse pressure index includes both the pulse pressure ΔP and a value calculated using the pulse pressure ΔP.

The pulse pressure calculation unit 53 may calculate an amplitude index and cause the display device 23 to display the amplitude index. As understood from the above description, the amplitude index and the resistance index calculated by the pulse pressure calculation unit 53 may be presented as independent indexes to a subject. Even in the configuration in which the amplitude index or the resistance index is calculated as an independent index, a cuff is not necessary in principle. Thus, it is possible to calculate each index with high precision while reducing a physical load on the subject.

(6) In each of the above-described embodiments, the pulse pressure calculation unit 53 (the resistance calculation unit 533) has calculated the ratio (SF/SM) of the blood mass integration value SM and the blood flow integration value SF as the resistance index, but a value calculated as the resistance index is not limited to the ratio (SF/SM). For example, a configuration in which the resistance index is calculated by substituting the ratio (SF/SM) to a predetermined function or a configuration in which the resistance index is calculated by multiplying the ratio (SF/SM) by a coefficient can also be adopted. For example, a configuration in which a difference between the blood mass integration value SM and the blood flow integration value SF is calculated as the resistance index can also be adopted. However, in the configuration in which the resistance index is calculated using the ratio of the blood mass integration value SM and the blood flow integration value SF, the resistance index can be calculated with high precision using the tendency that the ratio of the blood mass integration value SM and the blood flow integration value SF correlates with the pulse wave velocity.

(7) In each of the above-described embodiments, the pulse pressure calculation unit 53 (the amplitude calculation unit 531) has calculated the ratio (ΔF/ΔM) of the amplitude ΔF and the amplitude ΔM as the amplitude index, but a value calculated as the amplitude index is not limited to the ratio (ΔF/ΔM). For example, a configuration in which the ratio (ΔF/ΔM) is substituted to a predetermined function or a configuration in which the amplitude index is calculated by multiplying the ratio (ΔF/ΔM) by a coefficient can also be adopted. For example, a configuration in which a difference between the amplitude ΔF and the amplitude ΔM is calculated as the amplitude index can also be adopted. Here, in the configuration in which the amplitude index is calculated using the ratio of the amplitude ΔF and the amplitude ΔM, the amplitude index can be calculated with high precision using the tendency that the ratio (ΔF/ΔM) of the amplitude ΔM and the amplitude ΔF correlates to the blood flow rate. It is possible to calculate the amplitude index while reducing an influence of a skin thickness.

(8) In each of the above-described embodiments, the pulse pressure calculation unit 53 has used the temporal change MT in the blood mass index M during one analysis period T in the calculation of the pulse pressure ΔP, but the temporal change MT obtained by averaging the temporal changes MT in the blood mass index M in each of the plurality of analysis periods T over the plurality of analysis periods T may be used in the calculation of the pulse pressure ΔP. For the blood flow index F, the temporal change FT obtained by averaging the temporal changes FT in the blood flow index F in each of the plurality of analysis periods T over the plurality of analysis periods T may be used in the calculation of the pulse pressure ΔP.

(9) In each of the above-described embodiments, the pulse pressure calculation unit 53 (the resistance calculation unit 533) has normalized each of the blood mass index M and the blood flow index F within the normalization range equal to or greater than 0 and equal to or less than 1, but any upper limit and any lower limit of the normalization range can be used as long as the blood mass index M and the blood flow index F are normalized in a common range.

(10) In each of the above-described embodiments, the average blood pressure calculation unit 55 has calculated the average blood pressure Pave, but biological information calculated by the average blood pressure calculation unit 55 is not limited to the foregoing examples. For example, the average blood pressure calculation unit 55 can also calculate a value calculated by substituting the average blood pressure Pave to a predetermined function or a value obtained by multiplying the average blood pressure Pave by a coefficient. As understood from the foregoing description, the index calculated by the average blood pressure calculation unit 55 is comprehensively expressed as an index related to the average blood pressure Pave (hereinafter referred to as an "average blood pressure index"), the average blood pressure index includes both the average blood pressure Pave and a value calculated using the average blood pressure Pave.

(11) In each of the above-described embodiments, the average blood pressure calculation unit 55 has calculated the average blood pressure Pave in accordance with the average value obtained by averaging the blood vessel diameter indexes (the blood mass indexes M or the absorbance indexes J) during the analysis period T and the average value Fave obtained by averaging the blood flow indexes F during the analysis period T, but a method of calculating the average blood pressure Pave is not limited to the foregoing example. A configuration in which a time length of the analysis period T in which the blood vessel diameter indexes are averaged is caused to be different from a time length of the analysis period T in which the blood flow indexes F are averaged or a configuration in which the analysis period T in which the blood vessel diameter indexes are averaged does not overlap the analysis period T in which the blood flow indexes F are averaged on the time axis can be adopted.

In each of the above-described embodiments, the average blood pressure calculation unit 55 has calculated the average value Mave by averaging the plurality of blood mass indexes M within the analysis period T and has calculated the average value Fave by averaging the plurality of blood flow indexes F, but methods of calculating the average value Mave and the average value Fave are not limited to the foregoing example. For example, the average value Mave and the average value Fave may be calculated by calculating the average intensity spectrum by averaging the plurality of intensity spectra calculated at time points different within the analysis period T to calculate the average intensity spectrum and performing the calculation in the average intensity spectrum. The average value Jave can also be similarly calculated from the average intensity spectrum. When the average intensity $<I^2>$ is changed within the analysis period T, there is a possibility of the average blood pressure Pave not being appropriately calculated in the configuration in which the average intensity spectrum is used. Accordingly, even when the average intensity $<I^2>$ is changed, a configuration in which the average value Mave and the average value Fave are calculated at each time point within the analysis period T is appropriate, as exemplified in the above-described first embodiment, from the viewpoint of calculating the average blood pressure Pave with high precision.

(12) In each of the above-described embodiments, the biological analysis device 100 configured as a single device has been described, but as will be exemplified below, the plurality of components of the biological analysis device 100 can be realized as mutually separate devices. In the following description, an element calculating the systolic blood pressure Pmax and the diastolic blood pressure Pmin from the detection signal Z is referred to as a "calculation processing unit 27". The calculation processing unit 27 includes, for example, the components exemplified in FIG. 3 (the calculation unit 51A, the calculation unit 51B, the pulse pressure calculation unit 53, the average blood pressure calculation unit 55, and the blood pressure calculation unit 57). In an embodiment other than the first embodiment, the calculation processing unit 27 is configured as a similar element.

Figure 39:
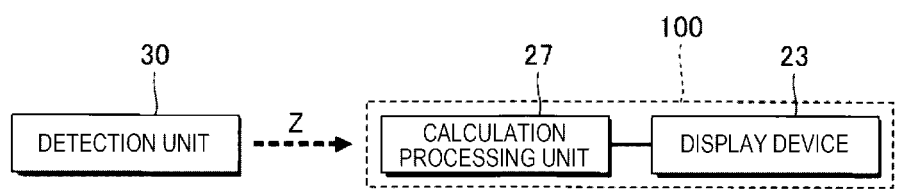
FIG. 39 is a diagram illustrating a configuration of a biological analysis device according to a modification example.

In each of the above-described embodiments, the biological analysis device 100 including the detection units 30 (30A, 30B, . . . ) has been exemplified, but as exemplified in FIG. 39, the detection unit 30 is assumed to be separate from the biological analysis device 100. The detection unit 30 is, for example, a portable optical sensor module that is worn on the measurement region H such as a wrist, an upper wrist, or the like of a subject. The biological analysis device 100 is realized as, for example, an information terminal such as a mobile phone or a smartphone. The biological analysis device 100 may be realized as a wrist watch type information terminal. The detection signal Z generated by the detection unit 30 is transmitted to the biological analysis device 100 in a wired or wireless manner. The calculation processing unit 27 of the biological analysis device 100 calculates the systolic blood pressure Pmax and the diastolic blood pressure Pmin from the detection signal Z and displays the systolic blood pressure Pmax and the diastolic blood pressure Pmin on the display device 23. As understood from the foregoing description, the detection unit 30 can be omitted from the biological analysis device 100.

Figure 40:
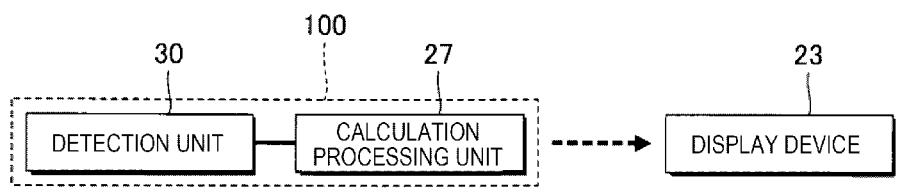
FIG. 40 is a diagram illustrating a configuration of a biological analysis device according to a modification example.

In each of the above-described embodiments, the biological analysis device 100 including the display device 23 has been exemplified, but as exemplified in FIG. 40, the display device 23 may be configured to be separate from the biological analysis device 100. The calculation processing unit 27 of the biological analysis device 100 calculates the systolic blood pressure Pmax and the diastolic blood pressure Pmin from the detection signal Z and transmits data for displaying the systolic blood pressure Pmax and the diastolic blood pressure Pmin to the display device 23. The display device 23 may be a dedicated display device, but may be mounted on, for example, an information terminal such as a mobile phone or a smartphone or a wrist watch type information terminal which can be carried by a subject. The systolic blood pressure Pmax and the diastolic blood pressure Pmin calculated by the calculation processing unit 27 of the biological analysis device 100 are transmitted to the display device 23 in a wired or wireless manner. The display device 23 displays the systolic blood pressure Pmax and the diastolic blood pressure Pmin received from the biological analysis device 100. As understood from the foregoing description, the display device 23 can be omitted from the biological analysis device 100.

Figure 41:
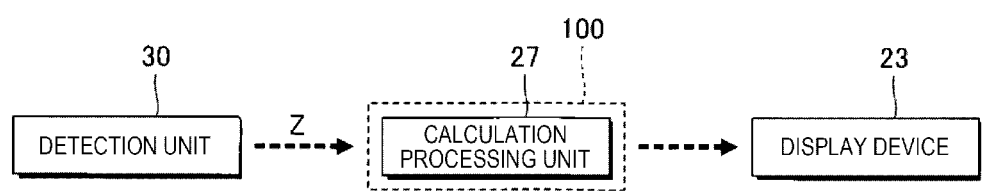
FIG. 41 is a diagram illustrating a configuration of a biological analysis device according to a modification example.

As exemplified in FIG. 41, the detection unit 30 and the display device 23 are assumed to be separate from the biological analysis device 100 (the calculation processing unit 27). For example, the biological analysis device 100

(the calculation processing unit 27) is mounted on an information terminal such as a mobile phone or a smartphone.

In the configuration in which the detection unit 30 is separate from the biological analysis device 100, the calculation unit 51A can also be mounted on the detection unit 30. The blood mass index M and the blood flow index F calculated by the calculation unit 51 are transmitted from the detection unit 30 to the biological analysis device 100 in a wired or wireless manner. As understood from the foregoing description, the index calculation unit 51A can be omitted from the biological analysis device 100.

(13) In each of the above-described embodiments, the wrist watch type biological analysis device 100 including the casing 12 and the belt 14 has been exemplified, but any specific form of the biological analysis device 100 can be used. For example, the biological analysis device 100 of any type such as a patch type which can be attached to the body of a subject, an ear-mounted type which can be mounted on the ears of a subject, a finger-mounted type (for example, a nail-mounted type) which can be mounted on a finger of a subject), or a head-mounted type which can be mounted on the head of a subject can be adopted. A handle type or grip type of biological analysis device 100 capable of measuring biological information when a subject holds the biological analysis device with his or her hands can also be adopted.

(14) In each of the above-described embodiments, the systolic blood pressure Pmax and the diastolic blood pressure Pmin of a subject has been displayed on the display device 23, but the configuration in which the subject is informed of the systolic blood pressure Pmax and the diastolic blood pressure Pmin is not limited to the foregoing example. For example, a subject can also be informed of the systolic blood pressure Pmax and the diastolic blood pressure Pmin by sound. In the ear-mounted type biological analysis device 100 which can be mounted on the ears of a subject, a configuration in which the subject is informed of the systolic blood pressure Pmax and the diastolic blood pressure Pmin by sound is particularly appropriate. The subject may not necessarily be informed of the pulse pressure $\Delta P$. For example, the systolic blood pressure Pmax and the diastolic blood pressure Pmin calculated by the biological analysis device 100 may be transmitted from a communication network to another communication device. The systolic blood pressure Pmax and the diastolic blood pressure Pmin may be stored in a portable recording medium detachably mounted on the storage device 22 of the biological analysis device 100 or the biological analysis device 100.

(15) The biological analysis device 100 according to each of the above-described embodiments is realized in cooperation with the control device 21 and a program, as exemplified above. The program according to a preferred aspect of the invention can be provided in a form stored a recording medium which can be read by the computer to be installed on the computer. The program stored in a recording medium included in a delivery server can also be provided to a computer in a form delivered via a communication network. The recording medium is, for example, a non-transitory recording medium. An optical recording medium (optical disc) such as a CD-ROM is a good example, but a recording medium with any known format such as a semiconductor recording medium or a magnetic recording medium can be included. The non-transitory recording medium includes any recording medium removing a transitory and propagating signal, and a volatile recording medium is not excluded.

The entire disclosures of Japanese Patent Application No. 2017-157162, filed Aug. 16, 2017 and Japanese Patent Application No. 2018-104934, filed May 31, 2018 are expressly incorporated by reference herein.

What is claimed is:

1. A biological analysis device comprising:
a first sensor that detects pulse pressure;
a second sensor that detects an average blood pressure;
a controller that is configured to:
calculate a pulse pressure index related to the pulse pressure of a biological body detected by the first sensor;
calculate an average blood pressure index related to the average blood pressure of the biological body detected by the second sensor; and
calculate a systolic blood pressure and a diastolic blood pressure in accordance with the pulse pressure index and the average blood pressure index,
wherein the pulse pressure index and the average blood pressure index are calculated in accordance with a blood flow index which is calculated from an intensity spectrum related to a frequency of light reflected and received from an inside of the biological body through radiation of a laser beam and is related to a blood flow of the biological body; and
a first detection device and a second detection device that each include a laser configured to radiate a laser beam to the biological body and a receiver configured to receive the laser beam reflected from an inside of the biological body,
wherein the controller is configured to calculate the pulse pressure index using a detection signal indicating a light reception level by the receiver of the first detection device,
wherein the controller is configured to calculate the average blood pressure index using a detection signal indicating a light reception level by the receiver of the second detection device,
wherein the blood flow index is calculated by integrating a product of intensity of each frequency in the intensity spectrum and the frequency within a predetermined frequency range,
wherein the controller is configured to calculate the pulse pressure index in accordance with a blood mass integration value obtained by integrating a blood mass index related to a blood mass of the biological body during an integration period and a blood flow integration value obtained by integrating the blood flow index during the integration period,
wherein the controller is configured to calculate the average blood pressure index in accordance with a blood vessel diameter index related to a blood vessel diameter of the biological body and the blood flow index, and
wherein the pulse pressure is expressed by the following equation, $$\Delta P = \rho \times PWV \times \Delta V$$

where $\Delta P$ is the pulse pressure, $\rho$ is a blood density, PWV is a pulse wave velocity, and $\Delta V$ is a blood flow rate amplitude.

2. The biological analysis device according to claim 1, wherein the biological analysis device is configured to be worn on an upper arm or a wrist of a biological body.

3. The biological analysis device according to claim 1, wherein the first detection device and the second detection device are configured to be provided at positions different in a circumferential direction of a limb of the biological body.

4. The biological analysis device according to claim 3, wherein the first detection device is configured to be worn on a surface of the upper arm of the biological body, and wherein the second detection device is configured to be installed on a surface of the upper arm opposite to the trunk.

5. The biological analysis device according to claim 3, wherein the first detection device is configured to be installed on a surface of a palm or a wrist of the biological body, and wherein the second detection device is configured to be installed on a surface of a back of the wrist.

6. A biological analysis method comprising:
calculating a pulse pressure index related to a pulse pressure of a biological body detected by a first sensor;
calculating an average blood pressure index related to an average blood pressure of the biological body detected by a second sensor; and
calculating a systolic blood pressure and a diastolic blood pressure in accordance with the pulse pressure index and the average blood pressure index,
wherein the pulse pressure index and the average blood pressure index are calculated in accordance with a blood flow index which is calculated from an intensity spectrum related to a frequency of light reflected and received from an inside of the biological body through radiation of a laser beam and is related to a blood flow of the biological body;
wherein a first detection device and a second detection device each include a laser configured to radiate a laser beam to the biological body and a receiver configured to receive the laser beam reflected from an inside of the biological body,
wherein the pulse pressure index is calculated using a detection signal indicating a light reception level by the receiver of the first detection device,
wherein the average blood pressure index is calculated using a detection signal indicating a light reception level by the receiver of the second detection device,
wherein the blood flow index is calculated by integrating a product of intensity of each frequency in the intensity spectrum and the frequency within a predetermined frequency range,
wherein the pulse pressure index is calculated in accordance with a blood mass integration value obtained by integrating a blood mass index related to a blood mass of the biological body during an integration period and a blood flow integration value obtained by integrating the blood flow index during the integration period,
wherein the average blood pressure index is calculated in accordance with a blood vessel diameter index related to a blood vessel diameter of the biological body and the blood flow index,
wherein the pulse pressure is expressed by the following equation, $$\Delta P = \rho \times PWV \times \Delta V$$

where $\Delta P$ is the pulse pressure, $\rho$ is a blood density, PWV is a pulse wave velocity, and $\Delta V$ is a blood flow rate amplitude, and
wherein the steps of calculating are performed by a controller.

7. A non-transitory computer readable storage medium that includes control logic that causes a controller to:
calculate a pulse pressure index related to a pulse pressure of a biological body detected by a first sensor;
calculate an average blood pressure index related to an average blood pressure of the biological body detected by a second sensor; and
calculate a systolic blood pressure and a diastolic blood pressure in accordance with the pulse pressure index and the average blood pressure index,
wherein the pulse pressure index and the average blood pressure index are calculated in accordance with a blood flow index which is calculated from an intensity spectrum related to a frequency of light reflected and received from an inside of the biological body through radiation of a laser beam and is related to a blood flow of the biological body,
wherein a first detection device and a second detection device each include a laser configured to radiate a laser beam to the biological body and a receiver configured to receive the laser beam reflected from an inside of the biological body,
wherein the pulse pressure index is calculated using a detection signal indicating a light reception level by the receiver of the first detection device,
wherein the average blood pressure index is calculated using a detection signal indicating a light reception level by the receiver of the second detection device,
wherein the blood flow index is calculated by integrating a product of intensity of each frequency in the intensity spectrum and the frequency within a predetermined frequency range,
wherein the pulse pressure index is calculated in accordance with a blood mass integration value obtained by integrating a blood mass index related to a blood mass of the biological body during an integration period and a blood flow integration value obtained by integrating the blood flow index during the integration period,
wherein the average blood pressure index is calculated in accordance with a blood vessel diameter index related to a blood vessel diameter of the biological body and the blood flow index, and wherein the pulse pressure is expressed by the following equation, $$\Delta P = \rho \times PWV \times \Delta V$$

where $\Delta P$ is the pulse pressure, $\rho$ is a blood density, PWV is a pulse wave velocity, and $\Delta V$ is a blood flow rate amplitude.

8. The biological analysis device according to claim 1, wherein the systolic blood pressure is expressed by the following equation, $$P_{max} = P_{ave} + \frac{2}{3}\Delta P$$

where $P_{max}$ is the systolic blood pressure, and $P_{ave}$ is the average blood pressure.

9. The biological analysis device according to claim 8, wherein the diastolic blood pressure is expressed by the following equation, $$P_{min} = P_{ave} - \frac{1}{3}\Delta P$$

where $P_{min}$ is the diastolic blood pressure.

* * * * *